(12) United States Patent
Barnes et al.

(10) Patent No.: US 7,819,807 B2
(45) Date of Patent: *Oct. 26, 2010

(54) BALANCE BODY ULTRASOUND SYSTEM

(75) Inventors: Stephanie A. Barnes, Bothell, WA (US); Steven M Bunce, Sedro Woolley, WA (US); Bryan S. Cabatic, Seattle, WA (US); Blake W. Little, Bothell, WA (US); Bill Purdue, Mill Creeek, WA (US); John D. Schultz, Issaquah, WA (US); Kari L. Rice, Bothell, WA (US)

(73) Assignee: SonoSite, Inc., Bothell, WA (US)

( * ) Notice: Subject to any disclaimer, the term of this patent is extended or adjusted under 35 U.S.C. 154(b) by 859 days.

This patent is subject to a terminal disclaimer.

(21) Appl. No.: 10/099,474

(22) Filed: Mar. 15, 2002

(65) Prior Publication Data

US 2003/0013966 A1     Jan. 16, 2003

Related U.S. Application Data

(63) Continuation-in-part of application No. 10/062,179, filed on Feb. 1, 2002, now Pat. No. 6,962,566, which is a continuation of application No. 09/840,002, filed on Apr. 19, 2001, now Pat. No. 6,569,101, and a continuation-in-part of application No. 09/630,165, filed on Aug. 1, 2000, now Pat. No. 6,416,475, which is a continuation-in-part of application No. 09/167,964, filed on Oct. 6, 1998, now Pat. No. 6,135,961, which is a continuation-in-part of application No. 08/863,937, filed on May 27, 1997, now Pat. No. 5,817,024, which is a continuation-in-part of application No. 08/826,543, filed on Apr. 3, 1997, now Pat. No. 5,893,363, which is a continuation-in-part of application No. 08/672,782, filed on Jun. 28, 1996, now Pat. No. 5,722,412.

(51) Int. Cl.
*A61B 8/00* (2006.01)

(52) U.S. Cl. .................. 600/443; 600/437; 600/459; 600/447

(58) Field of Classification Search ......... 600/437–463; 128/916

See application file for complete search history.

(56) References Cited

U.S. PATENT DOCUMENTS 3,626,417 A     12/1971     Gilbert (Continued)

FOREIGN PATENT DOCUMENTS

DE     2003/10224234     1/2003

(Continued)

OTHER PUBLICATIONS

Armitage et al., "An Integrated Array Transducer Receiver for Ultrasound Imaging", Sensors and Actuators, A 46-47 (a995), pp. 542-546.

(Continued)

*Primary Examiner*—Long V Le
*Assistant Examiner*—Sanjay Cattungal
(74) *Attorney, Agent, or Firm*—Fulbright & Jaworski L.L.P.

(57) ABSTRACT

The present invention relates to a hand held ultrasound system having a balance body, a transducer assembly connected to said balance body via a communication means and a plurality of control elements arranged in an ergonomic fashion on said balance body, such that a user may hold said system and operate at least one of said control elements with the same hand. In particular a medical ultrasound system comprising a balance body incorporating system electronics, a power supply and a user interface wherein the user interface comprises a D-controller and a touch screen and a transducer assembly attached to the balanced body by a cable. The present invention relates to a hand held ultrasound system having a balance body, a transducer assembly connected to said balance body via a communication means and a plurality of control elements arranged in an ergonomic fashion on said balance body, such that a user may hold said system and operate at least one of said control elements with the same hand. In particular a medical ultrasound system comprising a balance body incorporating system electronics, a power supply and a user interface wherein the user interface comprises a D-controller and a touch screen and a transducer assembly attached to the balanced body by a cable.

22 Claims, 23 Drawing Sheets

U.S. PATENT DOCUMENTS

| | | | |
|---|---|---|---|
| 3,964,296 A | 6/1976 | Matzuk | |
| 4,413,629 A | 11/1983 | Durley, III | |
| 4,649,930 A | 3/1987 | Groch et al. | |
| 5,293,351 A | 3/1994 | Noponen | |
| 5,295,485 A | 3/1994 | Shinomura et al. | |
| 5,373,317 A * | 12/1994 | Salvati et al. | 348/65 |
| 5,394,875 A | 3/1995 | Lewis et al. | |
| 5,427,111 A | 6/1995 | Traub et al. | |
| 5,465,011 A | 11/1995 | Miller et al. | |
| 5,555,534 A | 9/1996 | Maslak et al. | |
| 5,590,658 A | 1/1997 | Chiang et al. | |
| 5,617,864 A | 4/1997 | Stouffer et al. | |
| 5,634,465 A | 6/1997 | Schmeising et al. | |
| 5,647,366 A | 7/1997 | Weng | |
| 5,655,535 A | 8/1997 | Friemel et al. | |
| 5,709,209 A | 1/1998 | Friemel et al. | |
| 5,722,412 A | 3/1998 | Pflugrath et al. | |
| 5,795,297 A | 8/1998 | Daigle | |
| 5,817,024 A | 10/1998 | Ogle et al. | |
| 5,826,042 A | 10/1998 | Kirkendoll | |
| 5,839,442 A | 11/1998 | Chiang et al. | |
| 5,893,363 A | 4/1999 | Little et al. | |
| 5,935,074 A | 8/1999 | Mo et al. | |
| 6,048,319 A | 4/2000 | Hudgins et al. | |
| 6,083,156 A | 7/2000 | Lisiecki | |
| 6,095,980 A | 8/2000 | Burns et al. | |
| 6,126,608 A | 10/2000 | Kemme et al. | |
| 6,171,246 B1 * | 1/2001 | Averkiou et al. | 600/458 |
| 6,248,073 B1 | 6/2001 | Gilbert et al. | |
| 6,251,073 B1 | 6/2001 | Imran et al. | |
| 6,416,475 B1 | 7/2002 | Hwang et al. | |
| D462,446 S | 9/2002 | Felix et al. | |
| 6,447,451 B1 | 9/2002 | Wing et al. | |
| D467,002 S | 12/2002 | Felix et al. | |
| 6,490,684 B1 | 12/2002 | Fenstemaker et al. | |
| D469,539 S | 1/2003 | Felix et al. | |
| D469,877 S | 2/2003 | Felix et al. | |
| 6,530,887 B1 | 3/2003 | Gilbert et al. | |
| 6,532,152 B1 | 3/2003 | White et al. | |
| 6,561,979 B1 | 5/2003 | Wood et al. | |
| 6,569,101 B2 * | 5/2003 | Quistgaard et al. | 600/459 |
| 6,569,102 B2 | 5/2003 | Imran et al. | |
| 6,575,908 B2 * | 6/2003 | Barnes et al. | 600/443 |
| 6,618,206 B2 | 9/2003 | Tarakci et al. | |
| 6,663,567 B2 | 12/2003 | Ji et al. | |
| 6,685,645 B1 | 2/2004 | McLaughlin et al. | |
| 6,733,455 B2 | 5/2004 | Mo et al. | |
| 6,773,399 B2 | 8/2004 | Xi et al. | |
| 6,866,631 B2 | 3/2005 | McLaughlin et al. | |
| 6,866,632 B1 | 3/2005 | Chou et al. | |
| 6,896,658 B2 | 5/2005 | Ji et al. | |
| 6,936,008 B2 | 8/2005 | Tarakci et al. | |
| 6,962,566 B2 * | 11/2005 | Quistgaard et al. | 600/437 |
| 6,980,419 B2 | 12/2005 | Smith et al. | |
| 7,022,075 B2 * | 4/2006 | Grunwald et al. | 600/446 |
| 7,115,093 B2 * | 10/2006 | Halmann et al. | 600/437 |
| 2002/0169378 A1 * | 11/2002 | Mo et al. | 600/437 |
| 2002/0173344 A1 * | 11/2002 | Cupps et al. | 455/566 |
| 2002/0173721 A1 * | 11/2002 | Grunwald et al. | 600/437 |
| 2003/0004414 A1 | 1/2003 | McLaughlin et al. | |
| 2003/0009102 A1 * | 1/2003 | Quistgaard et al. | 600/446 |
| 2003/0013959 A1 * | 1/2003 | Grunwald et al. | 600/437 |
| 2003/0013965 A1 * | 1/2003 | Quistgaard et al. | 600/446 |
| 2004/0138569 A1 * | 7/2004 | Grunwald et al. | 600/459 |
| 2005/0131294 A1 | 6/2005 | Ji et al. | |
| 2006/0025684 A1 * | 2/2006 | Quistgaard et al. | 600/441 |
| 2006/0116578 A1 * | 6/2006 | Grunwald et al. | 600/440 |

FOREIGN PATENT DOCUMENTS

| | | |
|---|---|---|
| EP | 713102 | 5/1996 |
| EP | 763344 | 3/1997 |
| EP | 815793 | 1/1998 |
| WO | WO 94/23421 | 10/1994 |
| WO | WO 01/13796 | 3/2001 |
| WO | WO 2004/080364 | 9/2004 |

OTHER PUBLICATIONS

Hatfield et al., "High Frequency Ultrasound Scanning System", 38th Symposium on Circuits and Systems: Rio De Janeiro, Aug. 13-16, 1995, pp. 1175-1178 (1995).

Kim et al., "Pipelined Sampled-Delay Focusing in Ultrasound Imaging Systems", Ultrasonic Imaging, vol. 9, No. 2, Apr. 1987, pp. 75-91.

International Preliminary Examination Report, issued for PCT/US02/13386, dated Apr. 5, 2010, 7 pgs.

* cited by examiner

BALANCE BODY ULTRASOUND SYSTEM

CROSS-REFERENCES TO RELATED APPLICATIONS

This application is a continuation-in-part of U.S. Ser. No. 10/062,179 filed Feb. 1, 2002 now U.S. Pat. No. 6,962,566; which was a continuation of U.S. Ser. No. 09/840,002, filed Apr. 19, 2001, now U.S. Pat. No. 6,569,101; and is also a continuation-in-part of U.S. Ser. No. 09/630,165, filed Aug. 1, 2000, now U.S. Pat. No. 6,416,475; which was a continuation-in-part of U.S. Ser. No. 09/167,964, filed Oct. 6, 1998 now U.S. Pat. No. 6,135,961; which was a continuation-in-part of U.S. Ser. No. 08/863,937, filed May 27, 1997, now U.S. Pat. No. 5,817,024; which was a continuation-in-part of U.S. Ser. No. 08/826,543, filed Apr. 3, 1997, now U.S. Pat. No. 5,893,363; which was a continuation-in-part of U.S. Ser. No. 08/672,782, filed Jun. 28, 1996, now U.S. Pat. No. 5,722,412, the full disclosures of which are incorporated herein by reference.

BACKGROUND OF THE INVENTION

1. Field of the Invention

This invention relates to handheld ultrasound instruments having various diagnostic modes and transducer assemblies incorporating a balance body design, or other form factor to reduce strain of use during scanning procedures.

2. Description of the Prior Art

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand held ultrasonic scanhead that is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

The tendency has been the smaller systems also lose attributes of their larger stationary cousins due to limitations in space and power availability, the same factors that increase portability. An inverse relation exists between size and feature set. The use of digital beamformers and digital signal processing has allowed the expansion of capabilities of the smaller, more portable ultrasound systems relative to their predecessors. Recent releases of product like the SonoSite 180 have demonstrated the ability of manufacturers to reduce the size and weight of an ultrasound system while still delivering acceptable performance. As technology improves in both digital signal processing and power management, there remains a need for providing a hand held or portable ultrasound system that delivers acceptable performance characteristics, and at the same time is easy to use. There also remains a need for providing a method of being able to reduce costs to the users of ultrasound systems by providing an affordable and easily obtainable upgrade path to such user friendly ultrasound systems, both for hardware elements, and software.

BRIEF SUMMARY OF THE INVENTION

The present invention relates to hand held ultrasound systems providing the advances of digital signal processing and advanced human factors usability. The various design elements of the ultrasound systems presented herein are based on a series of common system electronics detailed in previously listed co-pending applications.

At its heart, the present invention provides a hand held ultrasound system having a balance body, a transducer assembly connected to said balance body via a communication means and a plurality of control elements arranged in an ergonomic fashion on said balance body, such that a user may hold said system and operate at least one of said control elements with the same hand.

In a second embodiment of the present invention, a medical ultrasound system comprising a balance body incorporating system electronics, a power supply and a user interface wherein said user interface comprises a D-controller and a touch screen and a transducer assembly attached to said balanced body via a cable. Control of the medical ultrasound device is achieved through selecting through a series of window menus either by using the D-controller or the touch screen or a combination of both. The second embodiment is lightweight and preferably weighs less than three and a half (3.50 lbs) pounds and the balance body can be held with the same hand that operates the D-controller. Optionally the system further comprises an I/O port for connecting to a docking station, and a handle.

In a third embodiment, we describe a lightweight diagnostic ultrasound instrument comprising a body having a power supply, a user interface for controlling the instrument, a display screen, and a system electronics package capable of a plurality of diagnostic ultrasound modes, said body weighing less than three pounds; a transducer assembly comprising a digital beam former, an A/D converter circuit, and a transducer array, the transducer assembly weighing less than one pound; and a wire connecting said body and said transducer assembly, the wire having a path for feeding power from the power supply to the transducer assembly, and a signal path for transmitting digital signals between the system electronics and the transducer assembly.

In a fourth embodiment we describe a wireless diagnostic ultrasound system comprising; a first body having system electronics, a user interface having a display screen and at least one control element, a first wireless transmit/receive element and a first power supply, said first body weighing less than two pounds; and a second body having a digital beam former, an A/D converter circuit, a transducer array, a second power supply, and a second transmit/receive element such that the digital beam former can be controlled by the system electronics via the first and second transmit/receive elements, said second body weighing less than one pound.

In still another embodiment, we describe a lightweight medical ultrasound system comprising a first body having system electronics, a first transmit/receive element and a first power supply, said first body weighing less than two pounds; a second body having a digital beam former, an A/D converter circuit, a transducer array, a second power supply, a second transmit/receive element and at least one control element, said second body weighing less than one pound; and a headset comprising a visual display, a receive element and a third power supply such that the first body, second body and head set are in communication with each other through the first and second transmit/receive element and the receive element so that a user may control the system through the at least one control element of the second body, while the first body performs the diagnostic operations through said system electronics, and the user may see the operations through the visual display of the head set.

In yet another embodiment, we describe a system as detailed above wherein the first body and the second body are incorporated into a single transducer assembly weighing less than two pounds and sharing a single power supply and having a single transmit/receive element.

Methods of using the various embodiments are also provided.

These and other embodiment of the present invention will become readily apparent upon a detailed inspection of the detailed description of the invention, and a study of the appended claims.

DETAILED DESCRIPTION OF THE INVENTION

Several terms have been clarified here to facilitate an understanding of the present invention.

Balance Body: A design for an ultrasound device wherein the center of gravity for the device is positioned close to the strength of a users hand. By shifting components around in the internal arrangement of the device, an aperture can be made in the device body where system electronics and other essential elements are, such that the device body is balanced for more comfortable holding in a users hand.

D-Controller: Any of a variety of control devices allowing a user to "point and click." The D-controller may be a digital directional controller (such as a four or eight directional controller), an analog "joy stick." The D-Controller allows a user to navigate an on-screen menu or displayed graphics similar to the use of a touch pad or lap top "nipple" pointing style device.

The present invention described a hand held ultrasound system having a balance body, a transducer assembly connected to said balance body via a connection means, and a plurality of control elements arranged in an ergonomic fashion on the balance body. The system is designed such that a user may hold the balance body and operate a key control element, such as a D-controller, with the same hand.

Figure 1A:
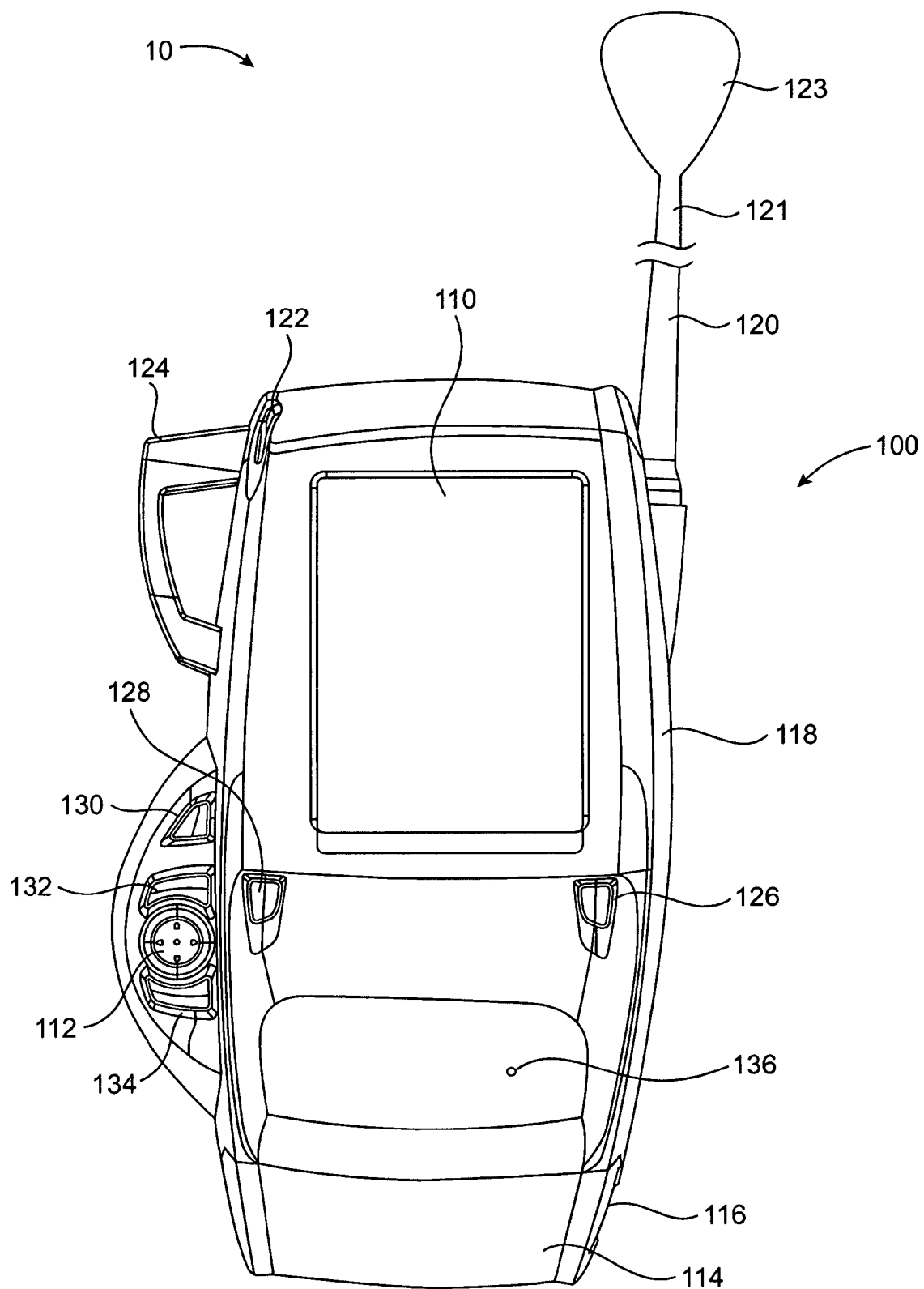
FIG. 1A-D illustrates a balance body ultrasound device of the present invention.
Figure 1B:
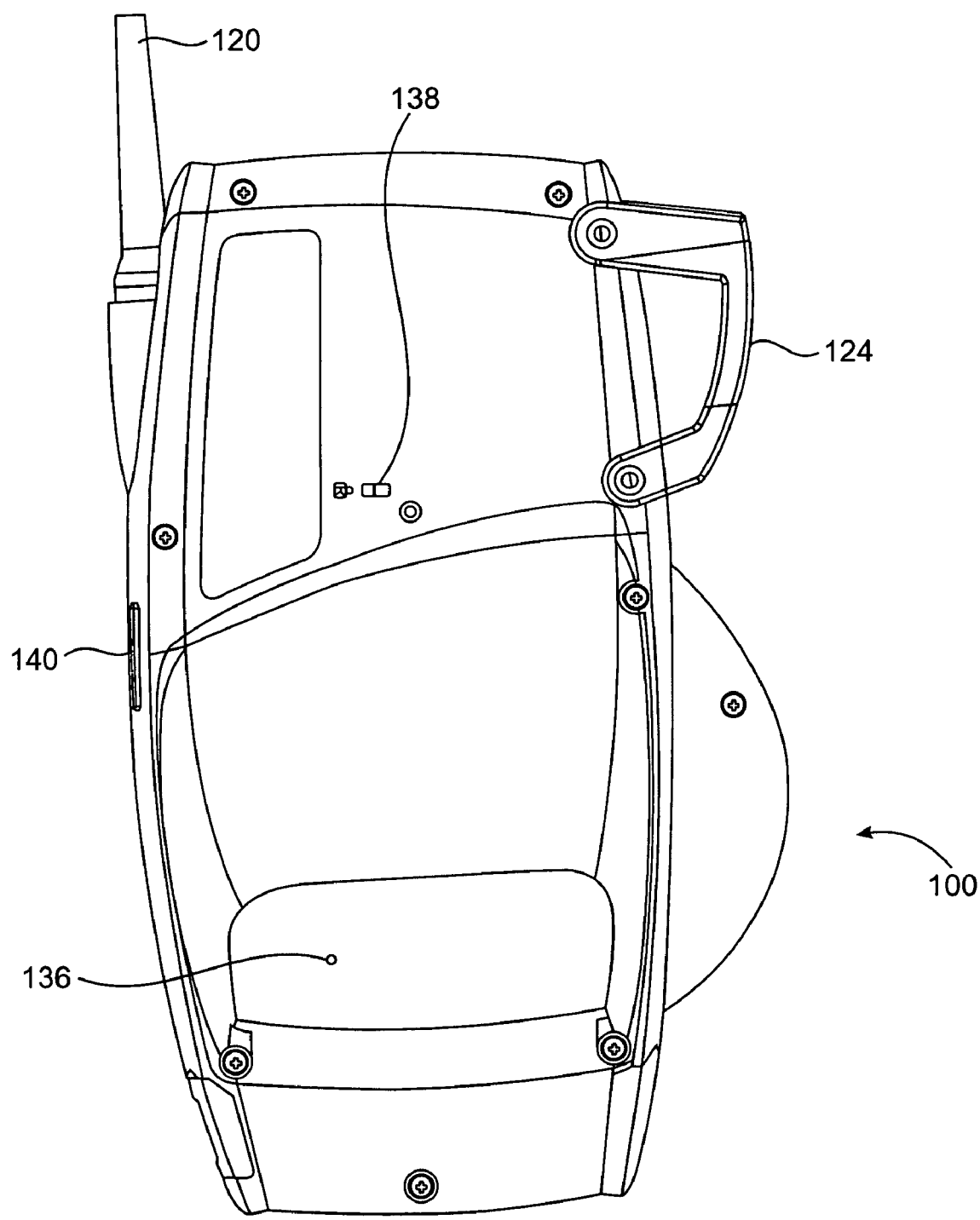
Figure 1C:
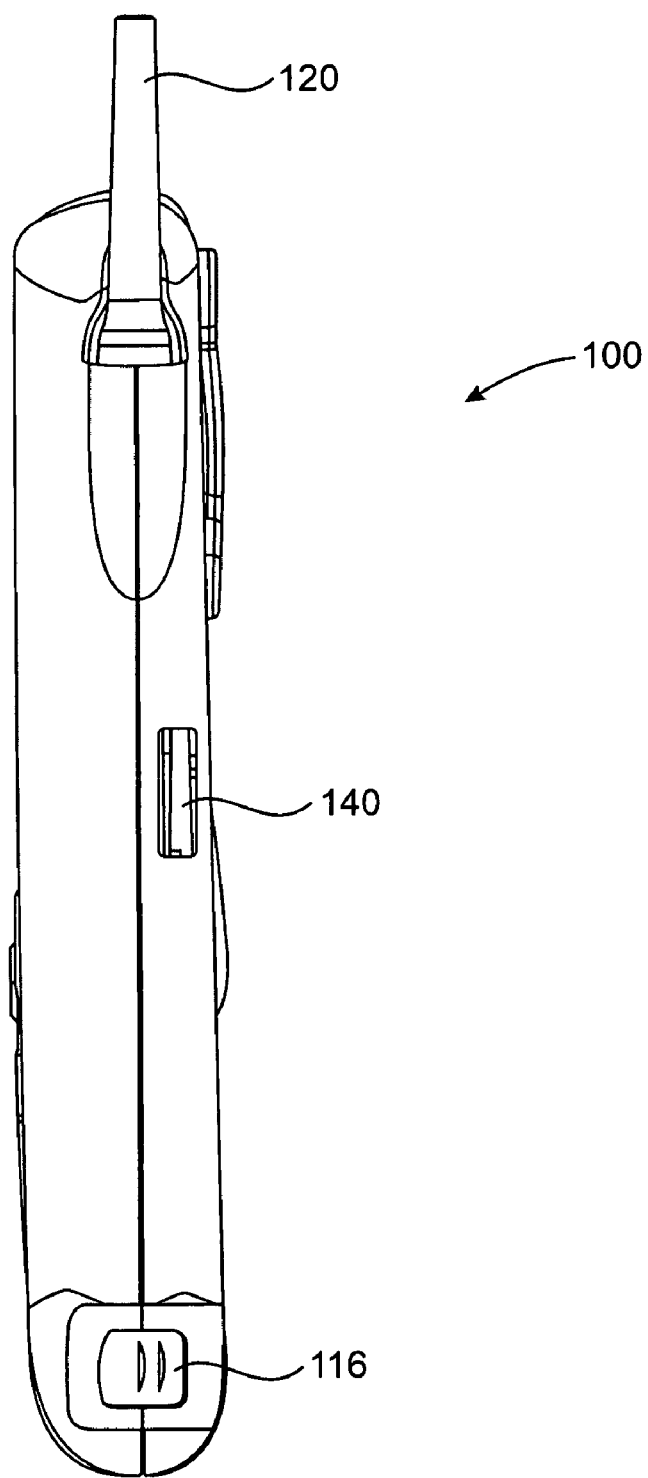

Turning now to FIGS. 1A-1C, a medical ultrasound system 10 comprises a balance body 100 incorporating system electronics, a power supply and a user interface wherein the user interface comprises a D-controller 112 and a touch screen 110, the transducer assembly 123 is connected to the balance body 100 via a cable 121 extending from a cable port 120.

The balance body 100 is a housing containing the system electronics, power supply and user interface. The balance body 100 has an aperture 136 through which a user may insert his or her hand. The aperture 136 is shaped to be comfortable for the majority of users. The balance body 100 has the aperture 136 for the users hand arranged so the users palm and fingers support the weight of the device by being essentially flat against the backside of the balance body 100. The users thumb wraps around to the front face of the balance body 100, and the D-controller 112 is positioned such that the users thumb can easily manipulate the D-controller 112 while the users palm and fingers support the weight of the balance body. In one embodiment, the power supply is located in the handle 114, opposite the system electronics (the aperture for a users hand being between the power supply and the system electronics). Since the power supply is one of the heavier element of the medical ultrasound system 10, the counter balancing effect makes the medical ultrasound system 10 easier to use and hold through the aperture 136. A power supply release button 116 is provided when necessary to remove the power supply within the handle 114.

A plurality of control elements or buttons 128, 132, 134 are also accessible to the users thumb, these control buttons or control elements are arrayed about the D-controller 112 so the user does not have to extend the thumb into an awkward position in order to actuate these control elements. Additional control elements 130, 126, such as the on/off switch 126 are purposefully positioned out of reach of the users thumb, thus avoiding inadvertently turning the system off during a medical scan. The control elements need not be buttons per se. The present invention can also operate using a series of touch pads that would supplement the primary D-controller 112, or utilize spring loaded dials that may be adjusted, then depressed below the surface of the balance body. The screen 110 is preferably a touch screen, and a stylus 122 is incorporated into the balance body 100 so a user may use the stylus 122, fingers (of the users second hand), or the D-controller 112 to input information through the touch screen 110. It should be noted here the D-controller 112 can also be used to position a pointer in a graphics image. In this manner a user may select an area of an image for enhanced viewing, or gain additional information about an icon on the screen or data about a scan image, or perform a manual trace of a scan image. The touch screen 110 has a plurality of image presentation styles, and among them is a QWERTY style keyboard so a user can input information such as patient data, or notes from an ultrasound scan.

The transducer assembly 123, or scan head comprises a transducer array and an inter-connector for coupling the transducer array to the cable. The transducer assembly 123 is connected to the balance body 100 by a cable 121 that feeds control signals to the transducer array (for steering, scan mode, etc.) as well as power from the power supply in the balance body 100. The transducer assembly 123 may be permanently affixed to the balance body through the cable 121, or the cable may be removable such that a different scan head/transducer assembly can be attached to the balance body.

Figure 7B:
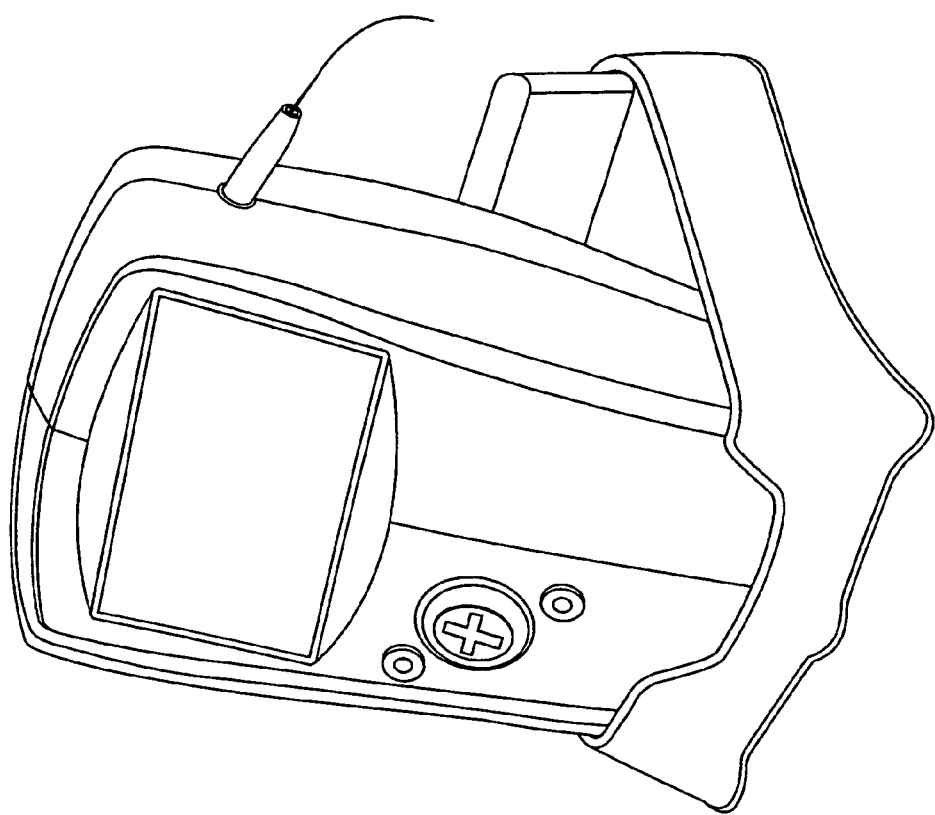
Figure 7A:
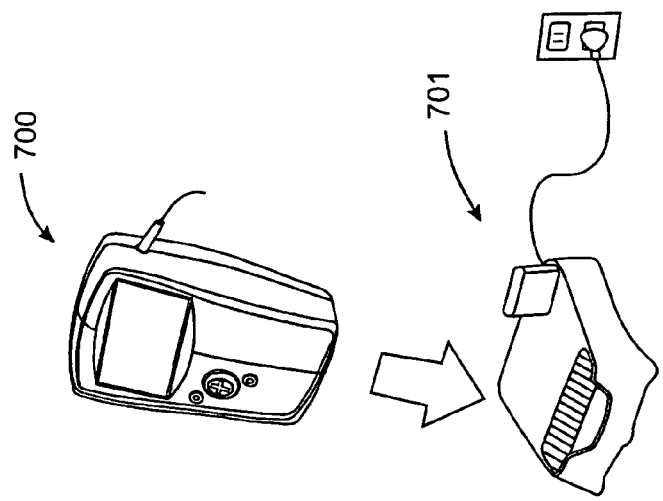
Figure 8:
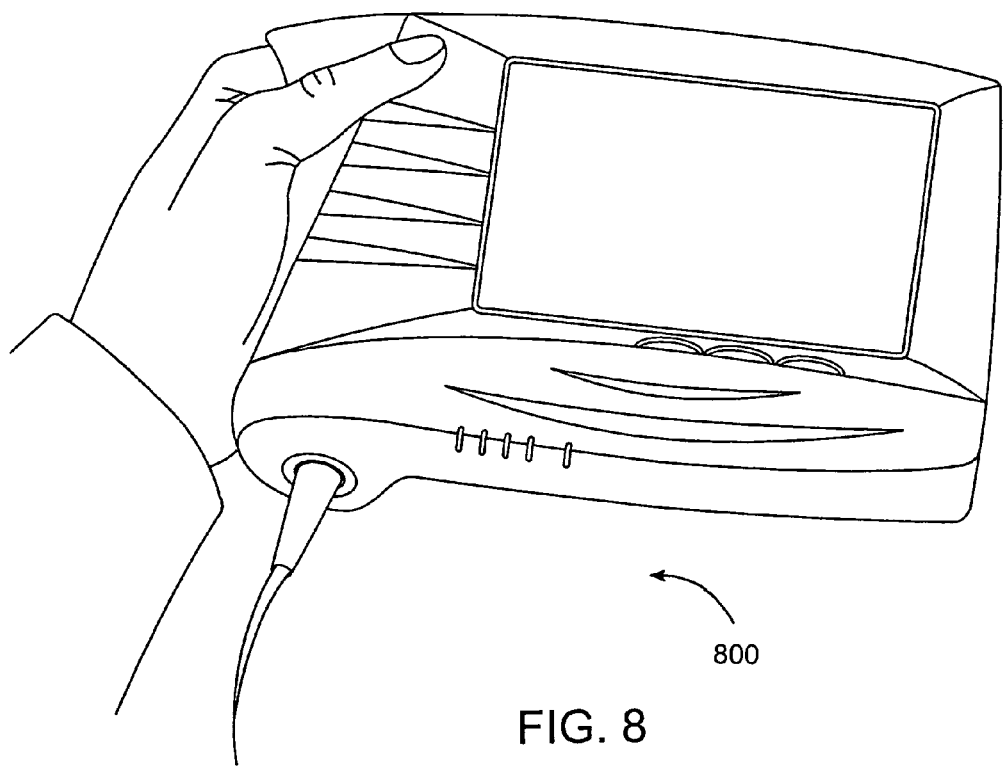
Figure 9:
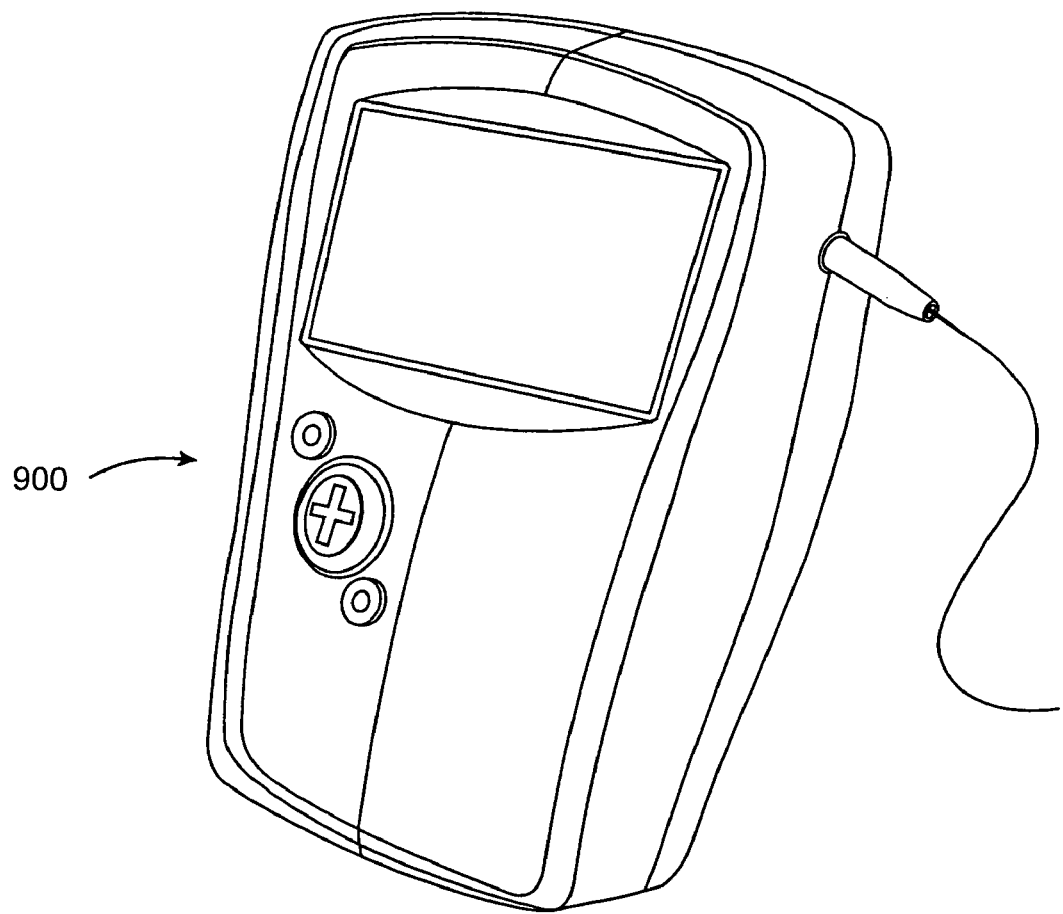
Figure 10:
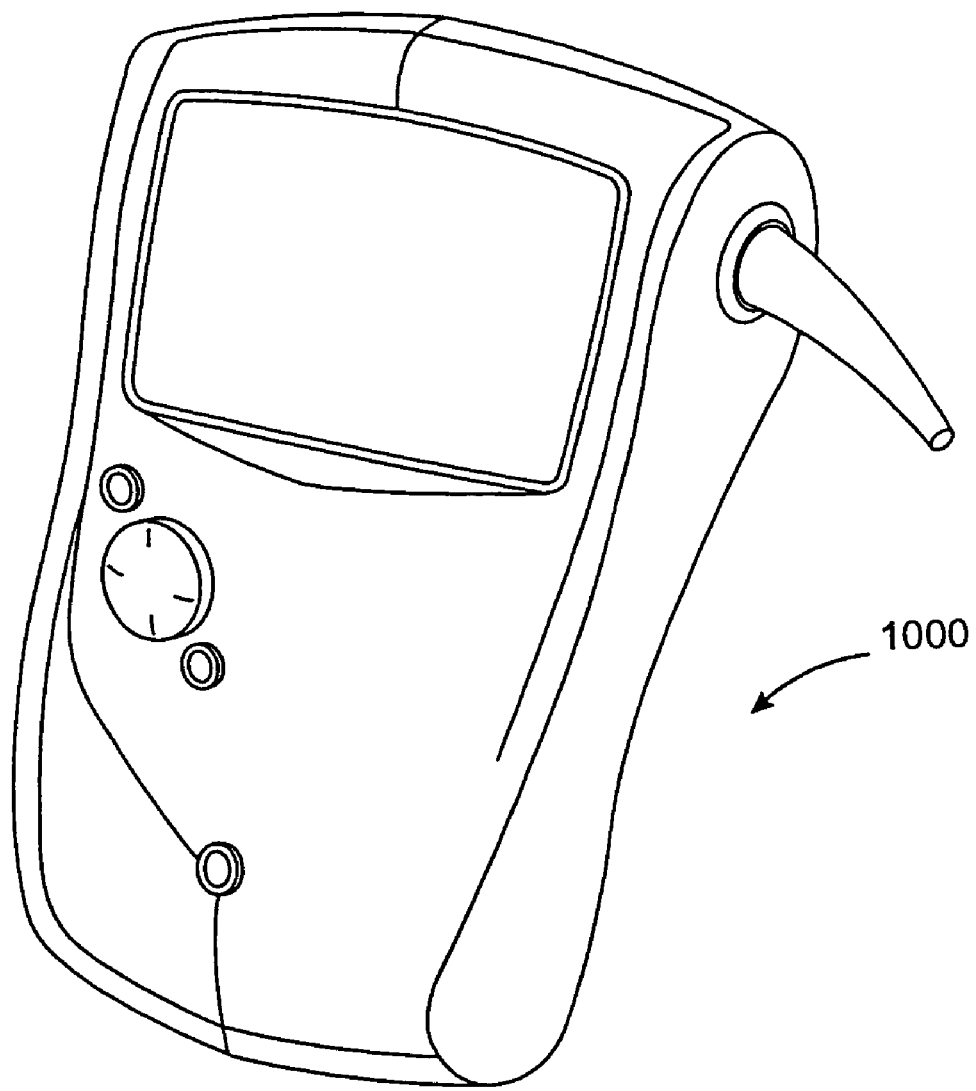
Figure 11:
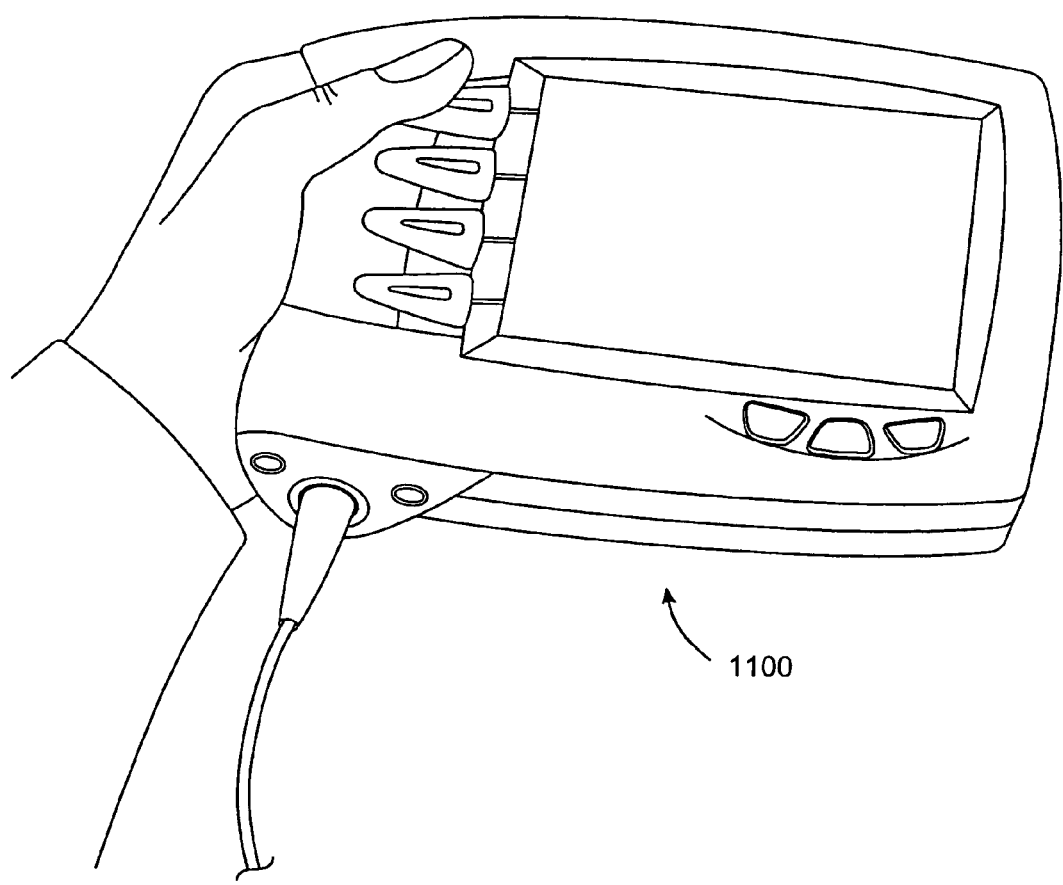
Figure 12:
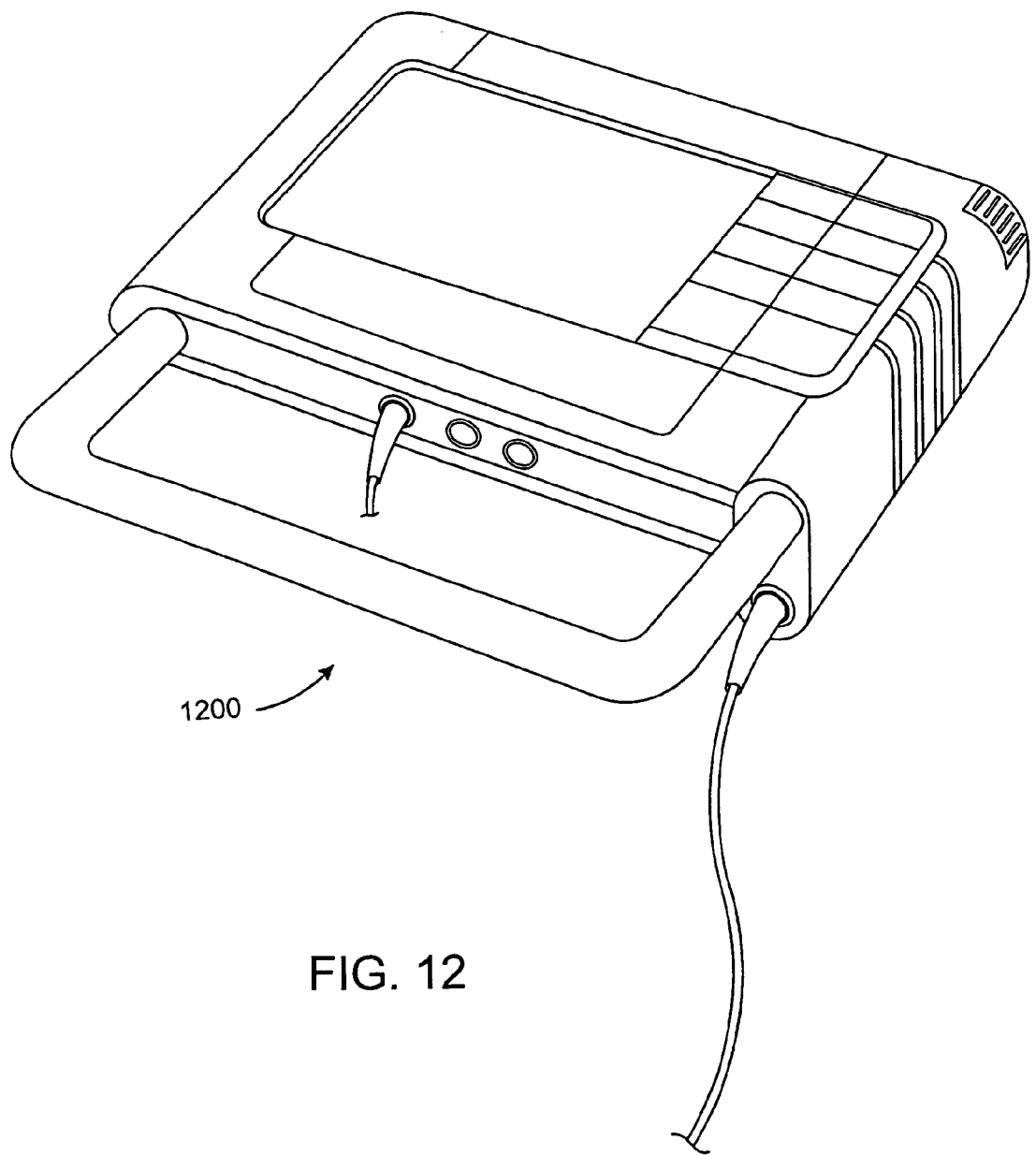

Additional features that may be incorporated onto the balance body include a holster 124 for retaining the transducer assembly 123 when not in use, a receptacle for placement of the stylus, an aperture 138 on the back side for connecting a locking pin into the balance body (when placed into a docking station), a spacer (not shown) for use in the aperture to accommodate smaller user hands and increase the user audience able to use the system and a hinge for the display screen so it can be tilted or swiveled. A data I/O port 140 is provided for communication with a docking station. Referring to FIGS. 7A & 7B, a balance body 700 is shown before (FIG. 7A) and after (FIG. 7B) insertion into a docking station 701. U.S. Pat. No. 6,416,475 teaches a PCMCIA data I/O port.

Dimensionally, the medical ultrasound system of the present embodiment has a total system weight under three and one half pounds (3.50 lbs). The cable is of varying length but is designed to be sufficient for a user to comfortably hold the balance body in the users field of view and scan a patient simultaneously. The balance body comprises the bulk of the weight while the transducer assembly generally weighs less than eight ounces (0.5 lbs). The balance body measures less than twelve inches long, seven inches in height and two inches in depth (12"×7"×2") not including the transducer assembly and attaching cable.

Figure 1D:
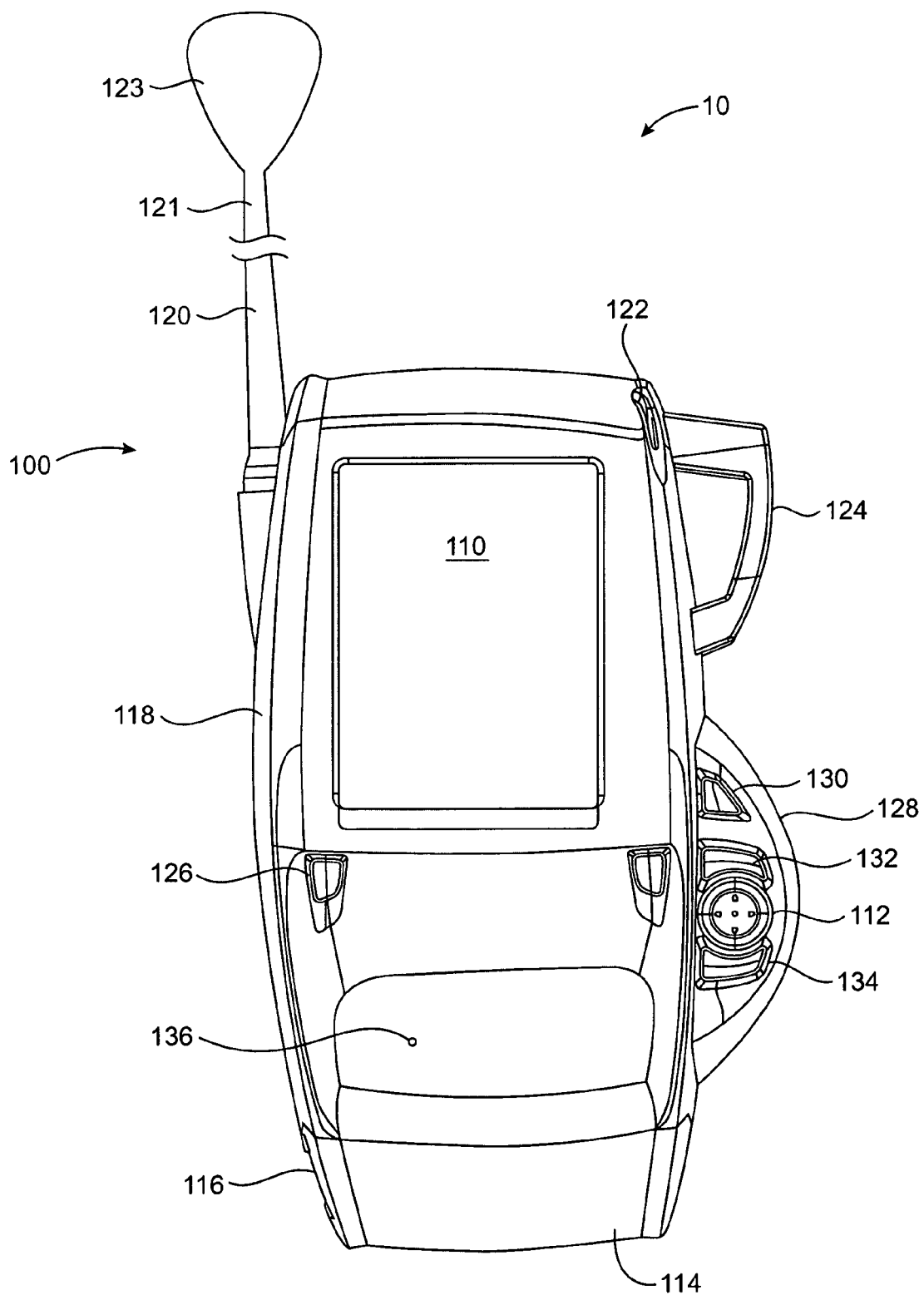
Figure 2:
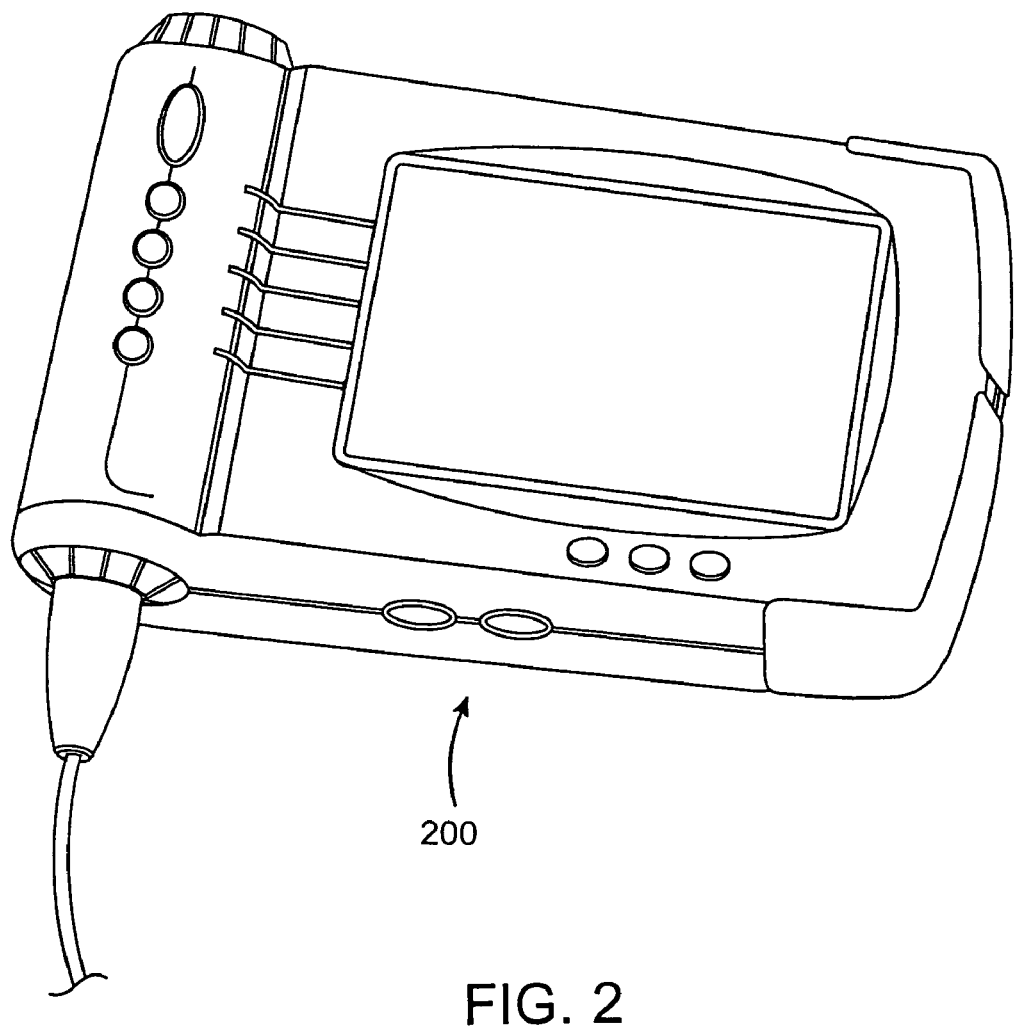
FIGS. 2-20 illustrate alternative embodiments of the present invention.
Figure 3:
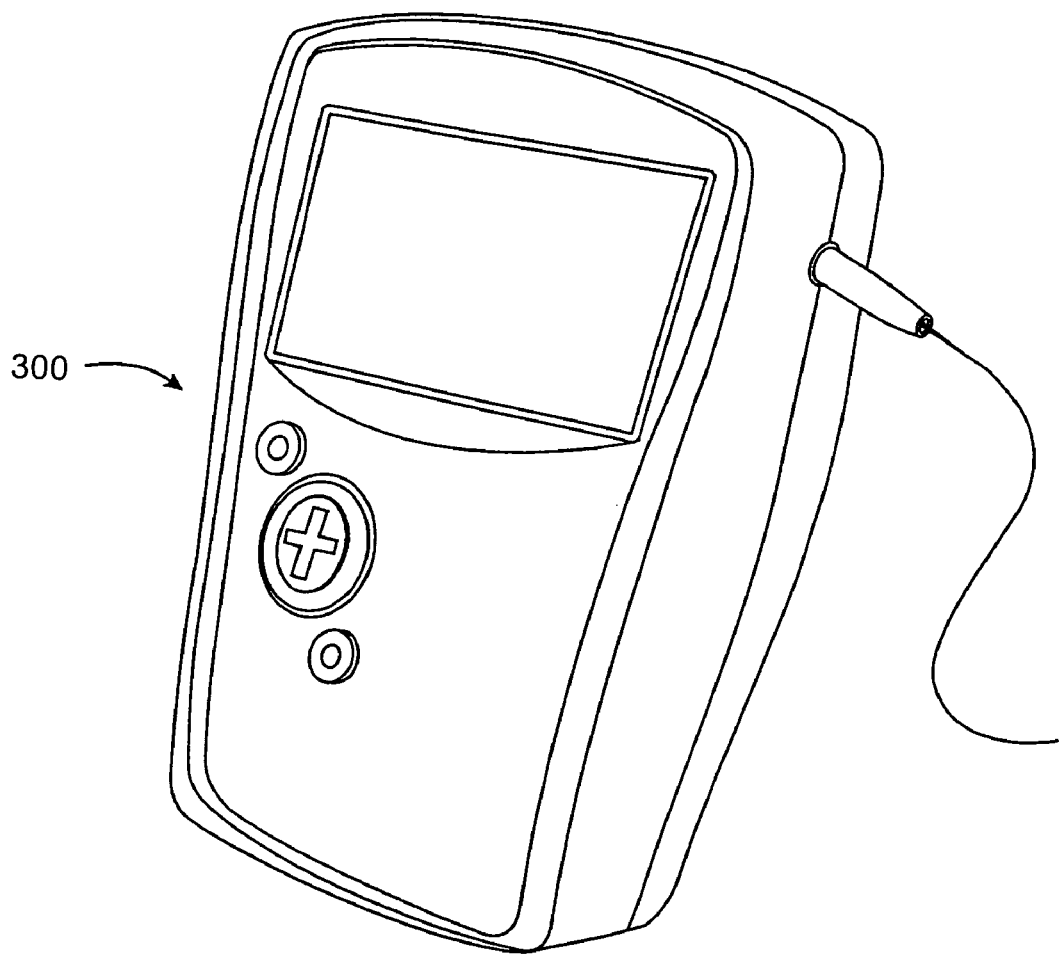
Figure 4:
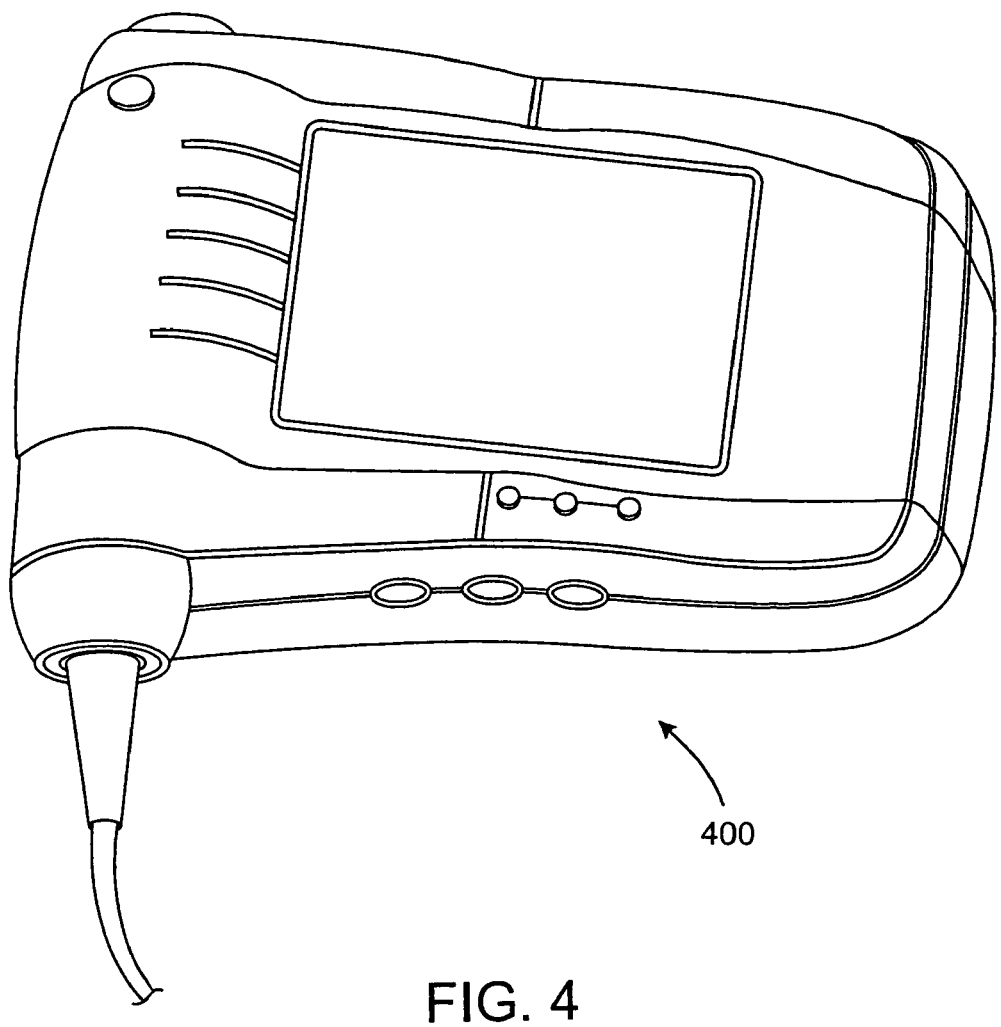
Figure 5:
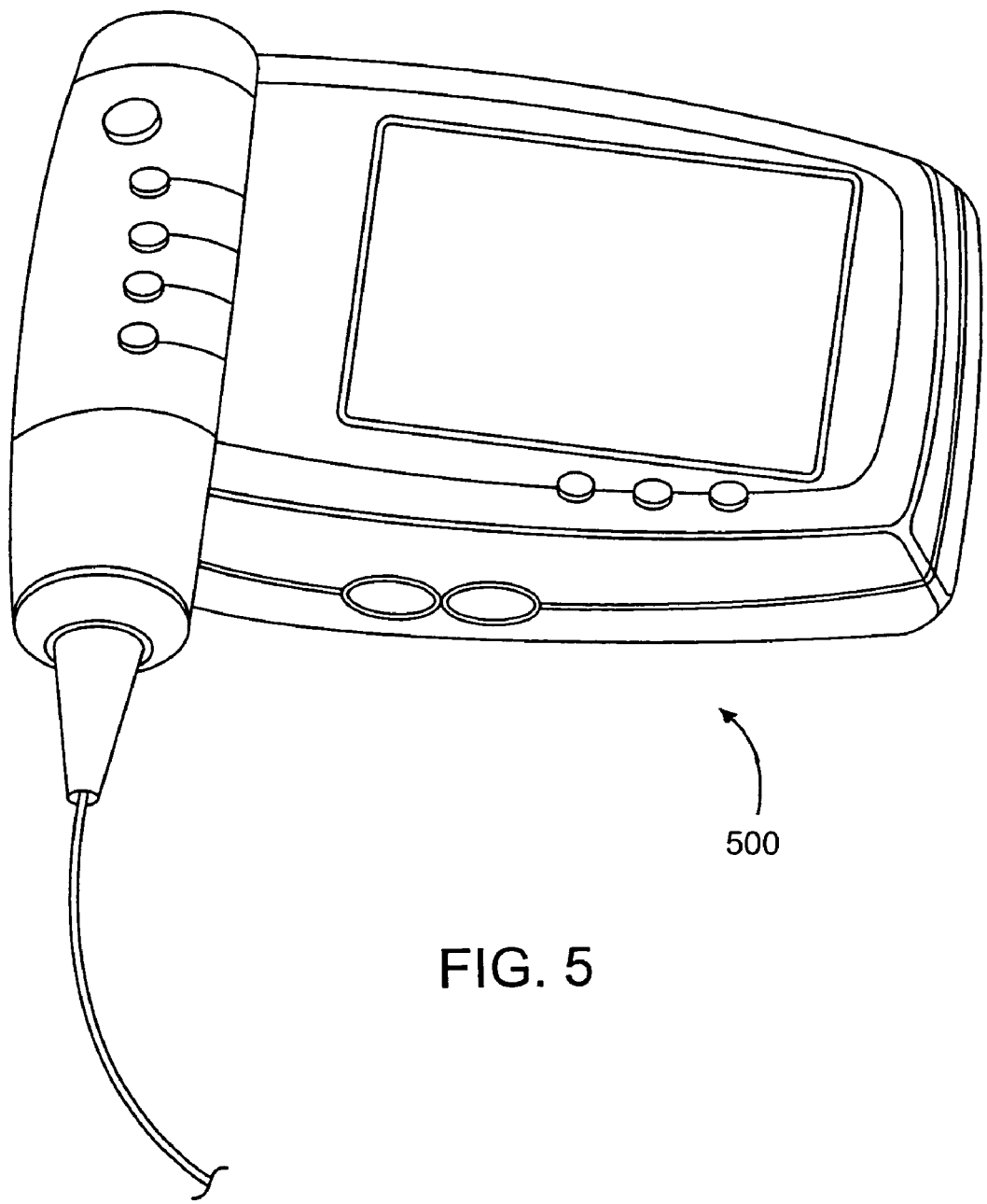
Figure 6:
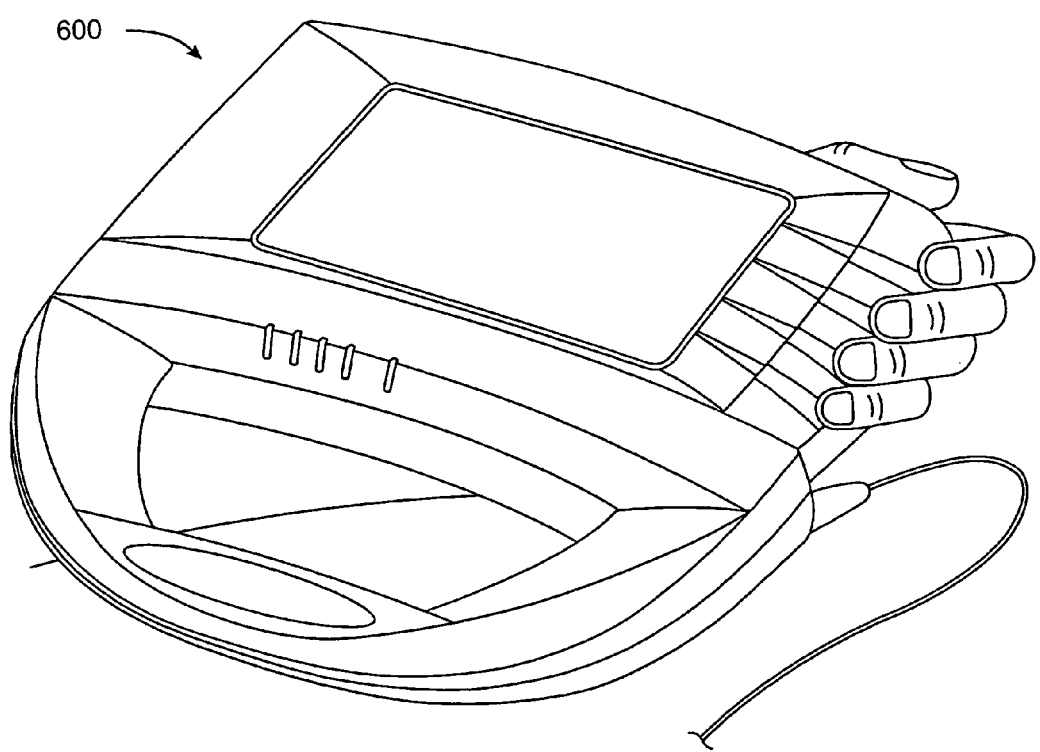
Figure 13:
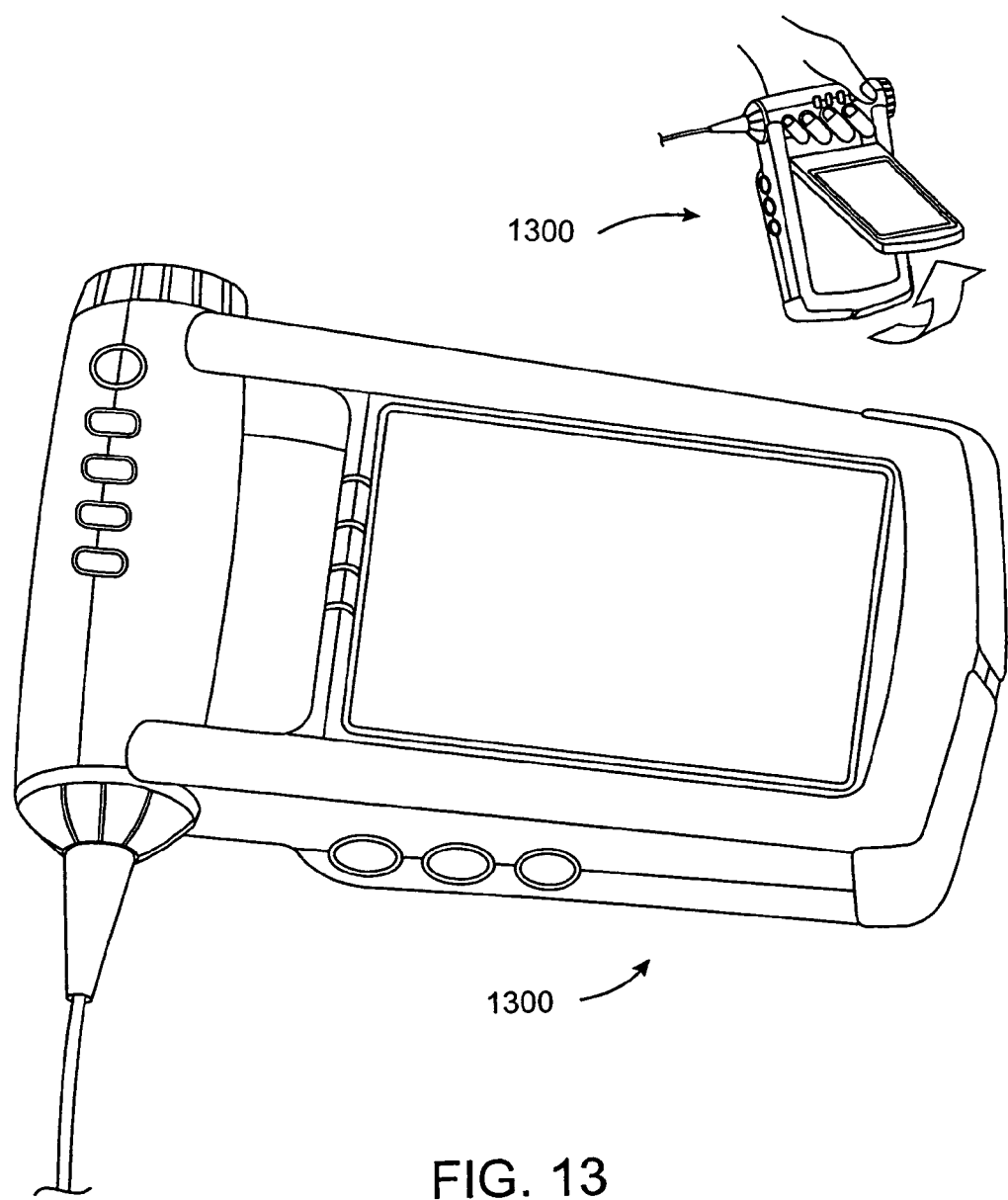
Figure 14:
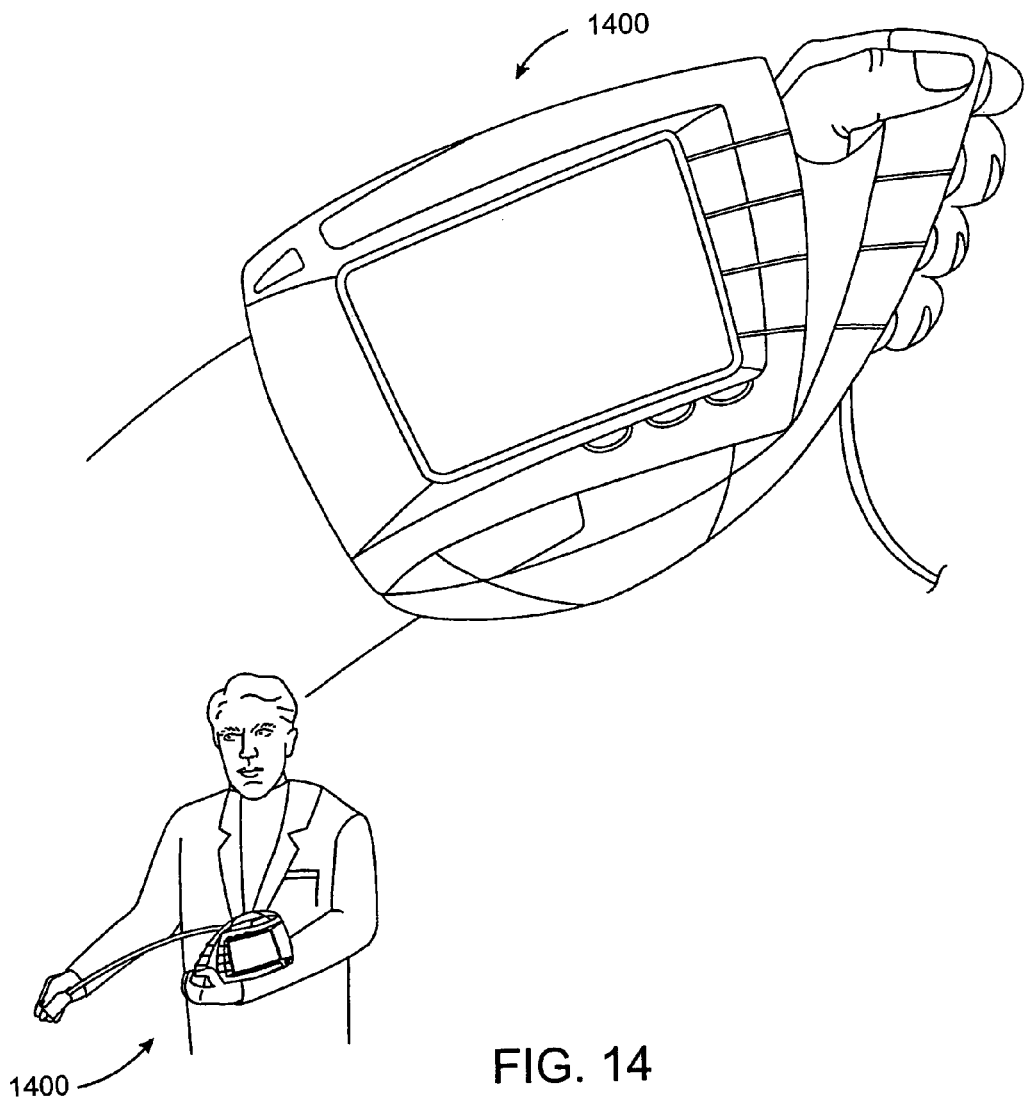
Figure 15:
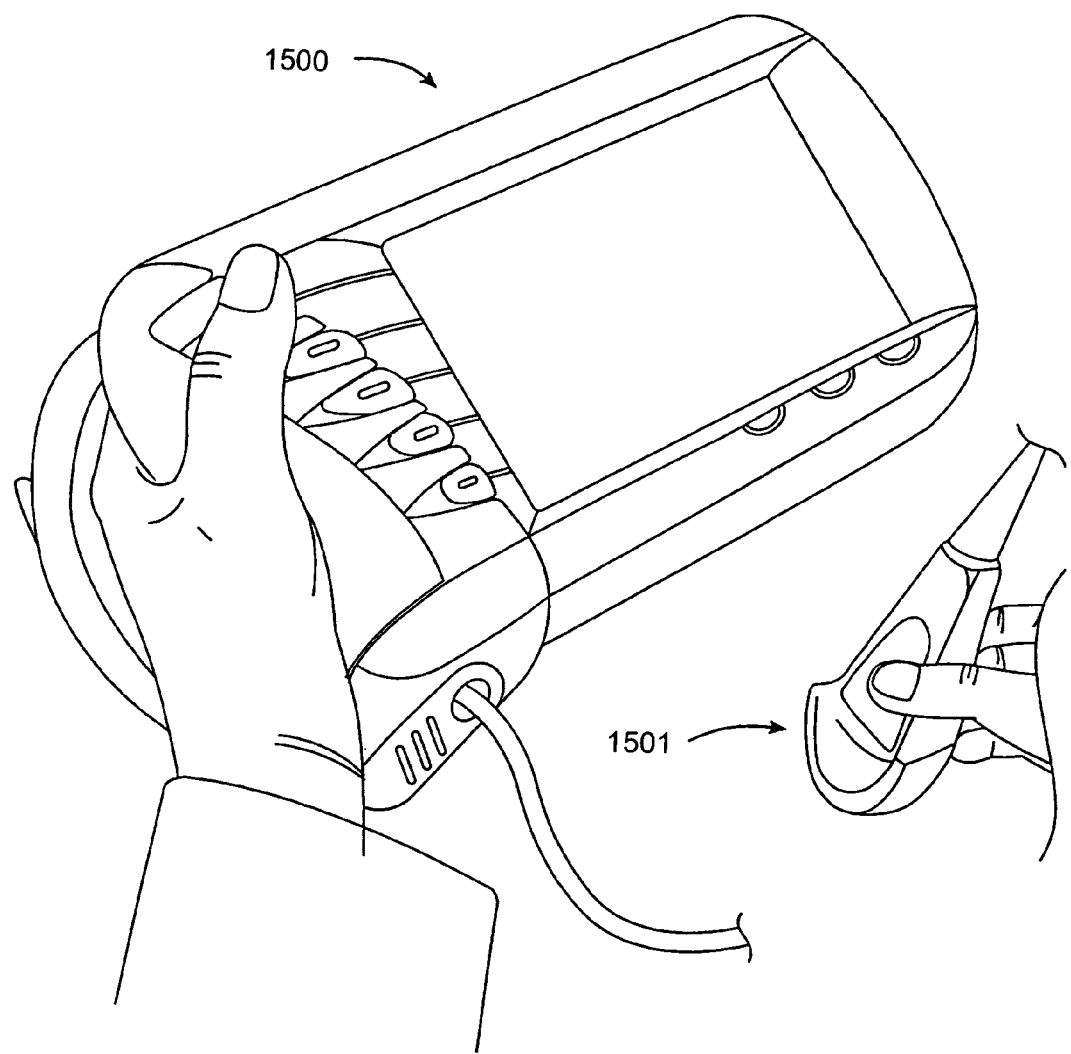
Figure 16:
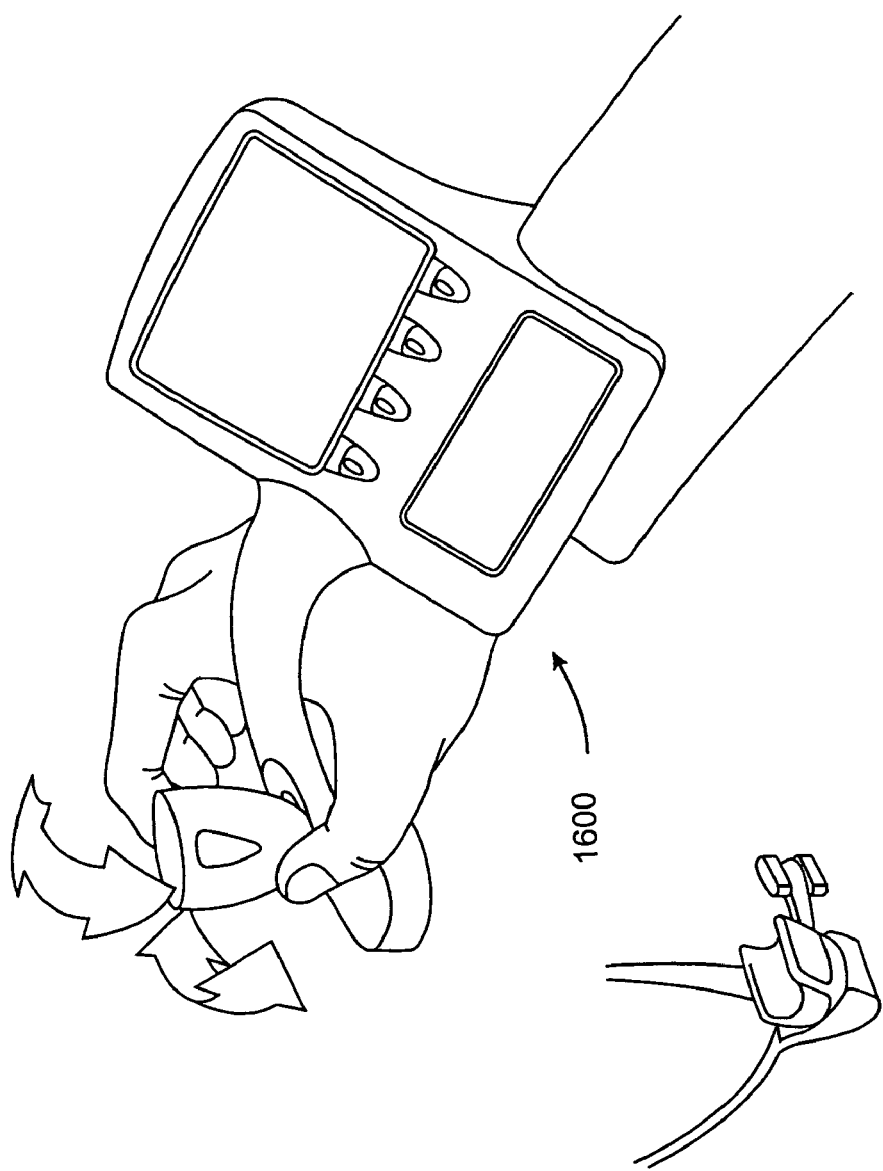
Figure 17:
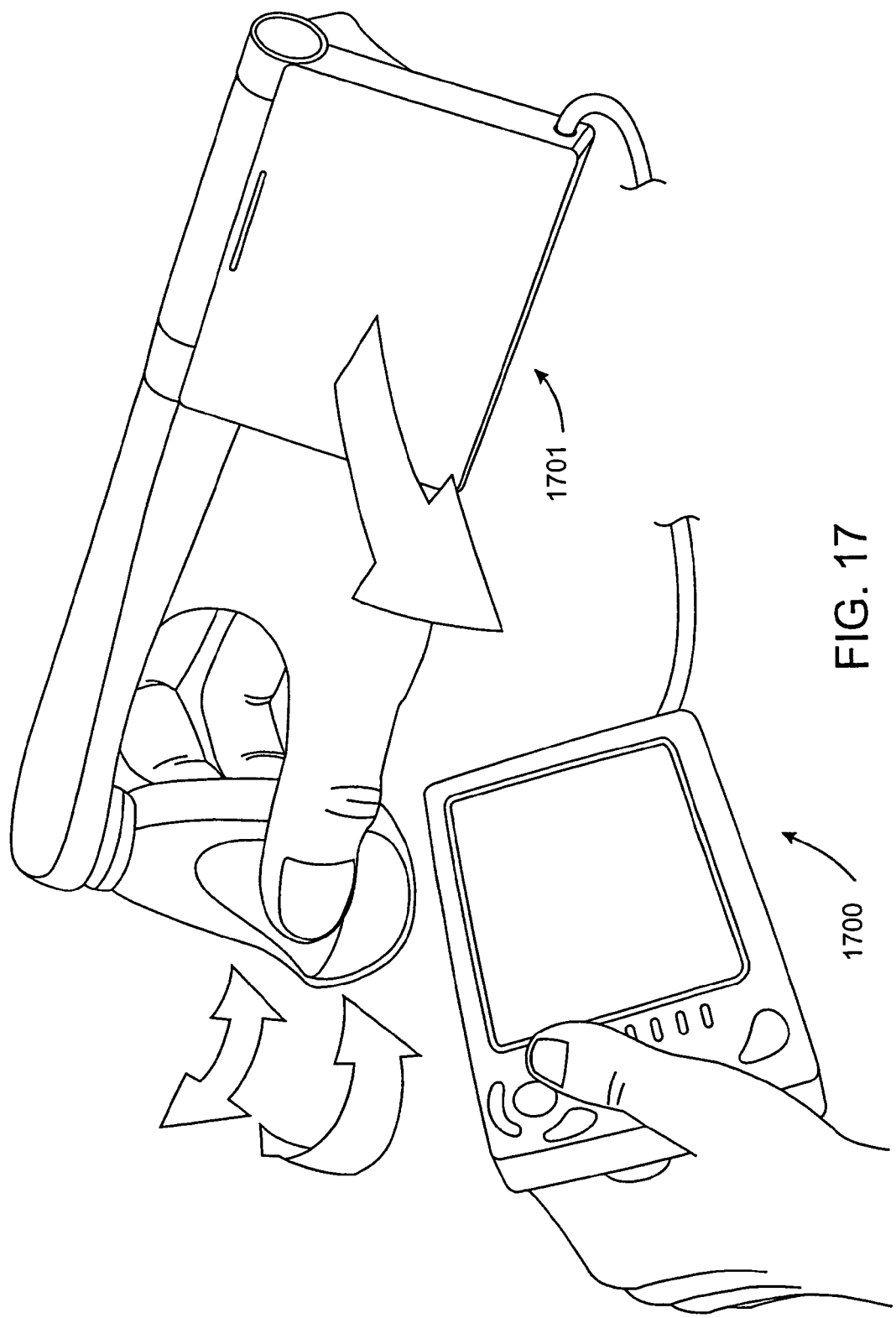
Figure 18:
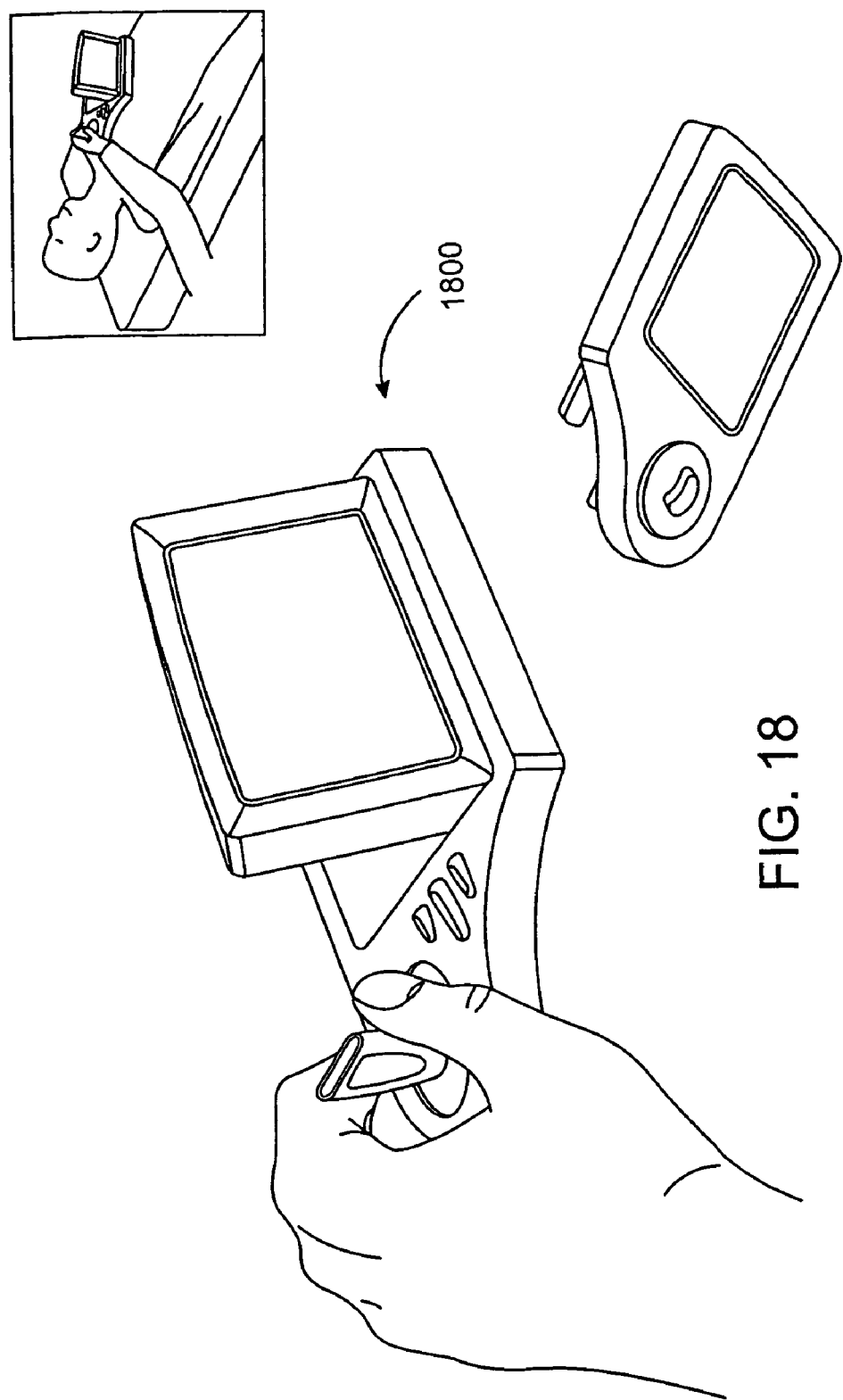

FIG. 1D illustrates a right-handed model of the present invention, where the controls are a mirror image of those in FIGS. 1A-C. FIGS. 2-6 and 8-17 show lightweight ultrasound instrument bodies (200, 300, 400, 500, 600, 800, 900, 1000, 1100, 1200, 1300, 1400, 1500, 1600, 1700). FIG. 13 shows an instrument body 1300 with an adjustable display screen. FIGS. 15 and 17 show an instrument body 1500, 1700 with a transducer 1501, 1701. FIG. 18 shows an instrument body 1800 having an integrated transducer assembly.

The medical ultrasound system also allows for the entry of a key code to permit upgrades to the software of the device. The operation of the key code is explained in greater detail in co-pending U.S. application Ser. No. 10/062,179 filed Feb. 1, 2002.

A second embodiment of the present invention forms a lightweight ultrasound instrument comprising a body having a power supply, a user interface for controlling the instrument, a display screen, and a system electronics package capable of a plurality of diagnostic ultrasound modes. In this embodiment, the body may optionally be a balance body. A transducer assembly is attached to the body via a wire or thin flexible cable, the transducer assembly comprises a digital beam former, an A/D converter circuit and a transducer array. The body, transducer assembly and wire combined weigh less than three pounds.

The wire connecting the body and transducer assembly provides power to the transducer assembly, and a signal path for the body and transducer assembly to communicate using digital data. In this manner the need for an analog cable, having many data paths for analog signals, is eliminated, and spares additional weight. The signal from the transducer array returns through the digital beam former incorporated into the transducer assembly so only digital information goes between the body and the transducer assembly.

The control elements of the lightweight ultrasound instrument are similar to those described above. A plurality of control elements, of which one is preferably a D-controller, and a touch screen. Again the body can be held with one hand, so the users thumb, or fingers can access the D-controller on the body.

In a third embodiment, a wireless diagnostic ultrasound system comprises a first body, and a second body. The first body is the main unit having system electronics, a user interface having a display screen and at least one control element, a first wireless transmit/receive circuit and a first power supply. The second body is a transducer assembly having a digital beam former, an A/D converter circuit, a transducer array, a second power supply and a second transmit/receive element such that the digital beam former of the second body can be controlled by the system electronics of the first body using the first and second transmit/receive circuits. The first and second transmit/receive circuits being a wireless means for communicating between the first body and the second body. Wireless data transfer and communication are well-understood technologies. Any standard wireless transmission standard capable of supporting the digital information communication of the present invention may be used.

The display screen in this embodiment is preferably a touch screen as well. The use of a touch screen permits the same advantages for ease of use to a user as previously described. A D-controller as one of the control elements allows for simple one-handed operation of the first body while the second hand holds the transducer assembly in place. The wireless design permits a user total freedom from encumbering cable and wire connections to the first body such that the transducer array can be positioned easily for manual steering.

Figure 19:
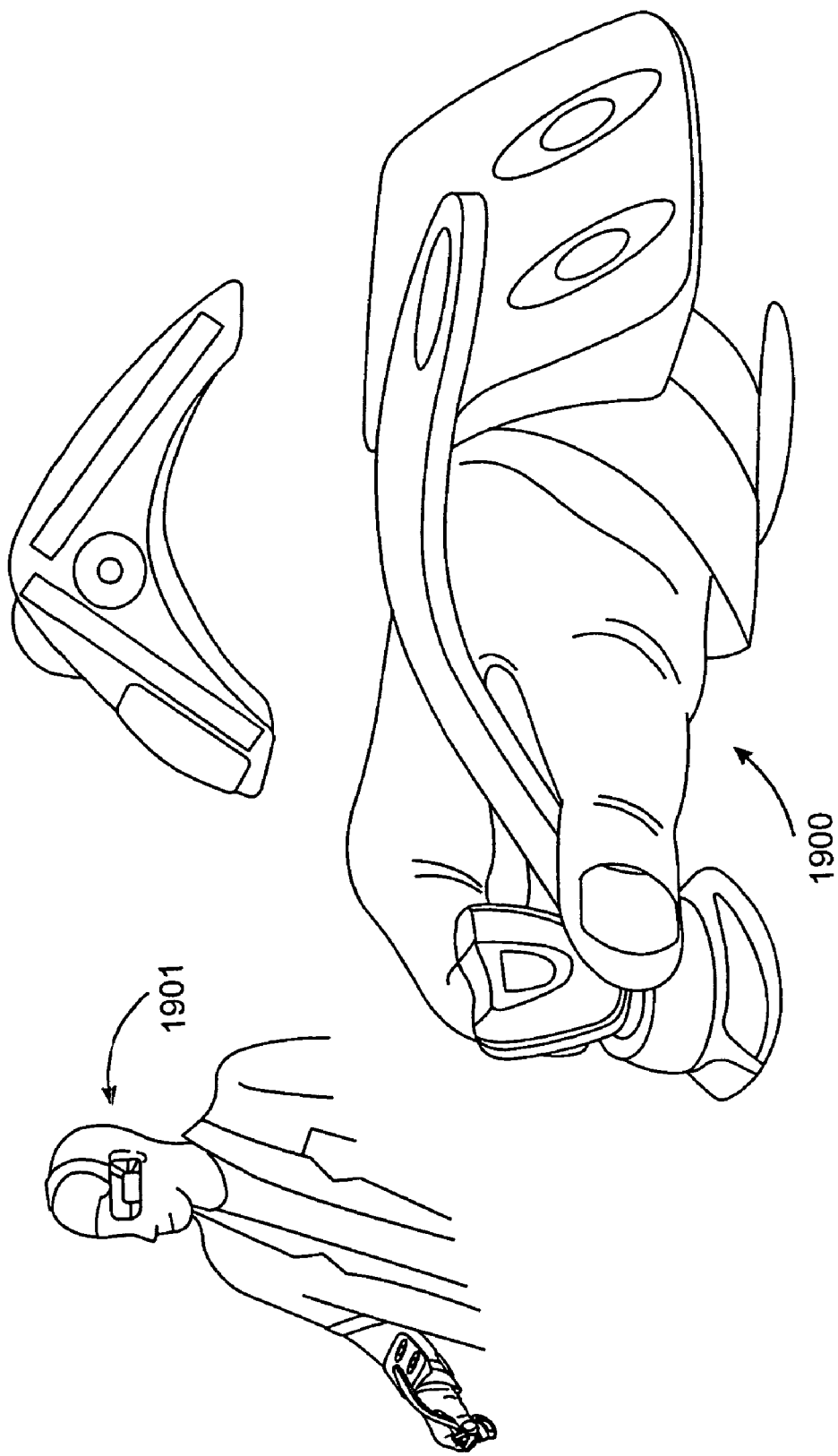
Figure 20:
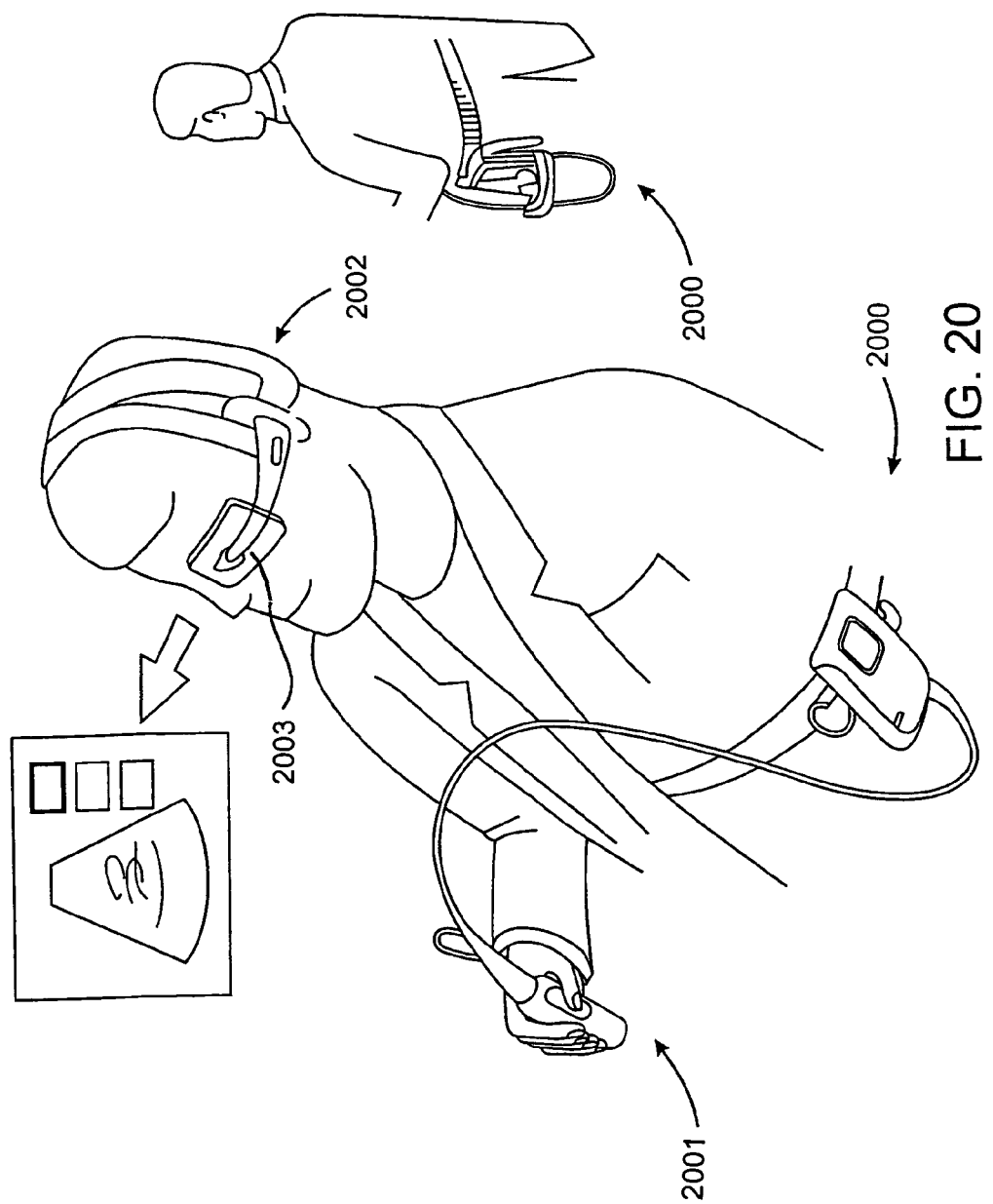

In a fourth embodiment, the invention comprises a first body having system electronics (FIG. 20 at 2000), a first transmit and receive element (FIG. 20 at 2001), and a first power supply. The first body weighs less than two pounds. A second body houses the transducer assembly. The transducer assembly has a digital beam former, an A/D circuit, a transducer array, a second power supply, a second transmit and receive element and at least one control element. The second body weighs less than one pound. A head set (FIG. 20 at 2002) is provided comprising a visual display (FIG. 20 at 2003), a receive element and a third power supply such that the first body, second body and head set are all in real time communication with each other. U.S. Pat. No. 5,817,024 describes that video information can be communicated from a video output in several television formats. The user can control the system through the second body or first body while visualizing the ultrasound scan through the head set. Voice recognition capability can be added to the head set through a head set microphone, allowing a user to command the operation of the ultrasound system at some level using voice activated commands instead of one or more of the manual control elements. FIG. 19 shows a medical ultrasound system where the first body and the second body are incorporated into a single transducer assembly 1900. A headset 1901 communicates wirelessly with single transducer assembly 1900.

Another embodiment of the invention may comprise a medical ultrasound system wherein an I/O port for connecting to a docking station further comprises a data path, a control path, and a power path for communicating with the docking station, such that data can move between said medical ultrasound system and the docking station, such that the medical ultrasound system can be controlled through the docking station, and such that the power supply can be recharged through the power path.

Yet another embodiment of the invention may comprise a medical ultrasound system comprising a balance body incorporating system electronics, a power supply and a user interface wherein the user interface comprises a D-controller and a touch screen and a transducer assembly attached to the balanced body via a cable. In this embodiment, the system electronics comprise a digital beam former, an image processor, and a first digital signal processor capable of processing B mode, M mode and flow (2D Doppler) scans. Some embodiments may comprise a second digital signal processor comprising a digital Doppler QBP filter for filtering PW Doppler signals and a digital signal processor core for PW Doppler signal processing. A description of a digital signal processor of this type is described in U.S. Pat. No. 6,569,101, incorporated herein by reference. In some embodiments, the first digital signal processor and the second digital signal processor are integrated into a single application specific integrated circuit (ASIC). A data storage means for ultrasound scans may be included. ASIC architecture is further described in Paragraphs 15, 50-54, 57-59, 63-65, and 67 of co-pending U.S. application Ser. No. 10/062,179, incorporated herein by reference.

Other embodiments may comprise a medical ultrasound system comprising a balance body incorporating system electronics, a power supply and a user interface wherein the user interface comprises a D-controller and a touch screen and a transducer assembly attached to the balanced body via a cable, the medical ultrasound system being a programmable diagnostic ultrasound instrument having a plurality of diagnostic modes. Other transducer and balance body assemblies are described in U.S. Pat. No. 6,416,475, incorporated by reference herein. Access to the diagnostic modes is controlled through a gate flag registry, the gate flag registry capable of modification through a verification procedure utilizing a secure means for extracting hidden bits from a keycode based on one or more unique system identifiers. Keycodes are further described in co-pending U.S. application Ser. No. 10/062,179, incorporated by reference herein.

What is claimed is:

1. A medical ultrasound system comprising:
   a balance body incorporating system electronics, a power supply and a user interface wherein said user interface comprises a D-controller and a touch screen; and
   a transducer assembly attached to said balanced body via a cable, said medical ultrasound system being a programmable diagnostic ultrasound instrument having a plurality of diagnostic modes, wherein access to the diagnostic modes is controlled through a gate flag registry, the gate flag registry configured to be modified through a verification procedure utilizing a secure means for extracting hidden bits from a keycode based on one or more unique system identifiers.

2. A lightweight diagnostic ultrasound instrument comprising:
   a body having a power supply, a user interface for controlling the instrument, a display screen, and a system electronics package configured to operate in a plurality of diagnostic ultrasound modes, said body weighing less than three pounds;
   a transducer assembly comprising a digital beam former, an A/D converter circuit, and a transducer array, the transducer assembly weighing less than one pound; and
   a wire connecting said body and said transducer assembly, the wire having a path for feeding power from the power supply to the transducer assembly, and a signal path for transmitting digital signals between the system electronics and the transducer assembly, said lightweight diagnostic ultrasound instrument being a programmable diagnostic ultrasound instrument having a plurality of diagnostic modes, wherein access to the diagnostic modes is controlled through a gate flag registry, the gate flag registry configured to be modified through a verification procedure utilizing a secure means for extracting hidden bits from a keycode based on one or more unique system identifiers.

3. A wireless diagnostic ultrasound system comprising:
   a first body having system electronics, a user interface having a display screen and at least one control element, a first wireless transmit/receive element and a first power supply, said first body weighing less than two pounds; and
   a second body having a digital beam former, an A/D converter circuit, a transducer array, a second power supply, and a second transmit/receive element such that the digital beam former can be controlled by the system electronics via the first and second transmit/receive elements, said second body weighing less than one pound, wherein the system electronics comprises a digital beam former, an image processor, and a first digital signal processor configured to process B mode, M mode and flow (2D Doppler) scans; and
   a second digital signal processor comprising:
      a digital Doppler QBP filter for filtering PW Doppler signals; and
      a digital signal processor core for PW Doppler signal processing, wherein the first digital signal processor and the second digital signal processor are integrated into a single application specific integrated circuit (ASIC).

4. The wireless diagnostic ultrasound system as described in claim 3, wherein said display screen is a touch screen.

5. The wireless diagnostic ultrasound system as described in claim 4, wherein the touch screen is configured to respond to a series of on screen commands and is re-programmable for hot menus.

6. The wireless diagnostic ultrasound system as described in claim 4, wherein the touch screen further comprises a QWERTY style keypad.

7. The wireless diagnostic ultrasound system as described in claim 3, wherein the at least one control element is a D-controller.

8. The wireless diagnostic ultrasound system as described in claim 3, wherein said first body can be held and operated with one hand.

9. The wireless diagnostic ultrasound of claim 3, further comprising a holster for retaining a transducer assembly.

10. A wireless diagnostic ultrasound system comprising:
    a first body having system electronics, a user interface having a display screen and at least one control element, a first wireless transmit/receive element and a first power supply, said first body weighing less than two pounds; and
    a second body having a digital beam former, an A/D converter circuit, a transducer array, a second power supply, and a second transmit/receive element such that the digital beam former can be controlled by the system electronics via the first and second transmit/receive elements, said second body weighing less than one pound, said wireless diagnostic ultrasound system being a programmable diagnostic ultrasound instrument having a plurality of diagnostic modes, wherein access to the diagnostic modes is controlled through a gate flag registry, the gate flag registry configured to be modified through a verification procedure utilizing a secure means for extracting hidden bits from a keycode based on one or more unique system identifiers.

11. A lightweight medical ultrasound system comprising:
    a first body having system electronics, a first transmit/receive element and a first power supply, said first body weighing less than two pounds;
    a second body having a digital beam former, an A/D converter circuit, a transducer array, a second power supply, a second transmit/receive element and at least one control element, said second body weighing less than one pound; and
    a headset comprising a visual display, a receive element and a third power supply such that the first body, second body and head set are in communication with each other through the first and second transmit/receive element and the receive element so that a user may control the system through the at least one control element of the second body, while the first body performs the diagnostic operations through said system electronics, and the user may see the operations through the visual display of the head set.

12. The lightweight medical ultrasound system as described in claim 11, wherein the first and second transmit/receive elements are wireless.

13. The lightweight medical ultrasound system as described in claim 11, wherein the receive element of the headset is wireless.

14. The lightweight medical ultrasound system as described in claim 11, wherein the first and second transmit/receive elements and the receive element of the headset are wired.

15. The lightweight medical ultrasound system as described in claim 14, wherein a first power supply in the first body also provides power to the second body and to the headset, the second power supply and the third power supply being omitted.

16. The lightweight medical ultrasound system as described in claim 11, wherein the first body and the second body are incorporated into a single transducer assembly weighing less than two pounds and sharing a single power supply and having a single transmit/receive element.

17. The medical ultrasound system as described in claim 11, wherein the system electronics comprises a digital beam former, an image processor, and a first digital signal processor capable of processing B mode, M mode and flow (2D Doppler) scans.

18. The medical ultrasound system as described in claim 17, having a second digital signal processor comprising:
    a digital Doppler QBP filter for filtering PW Doppler signals; and
    a digital signal processor core for PW Doppler signal processing.

19. The medical ultrasound system as described in claim 18, wherein the first digital signal processor and the second digital signal processor are integrated into a single application specific integrated circuit (ASIC).

20. The medical ultrasound system as described in claim 11, being a programmable diagnostic ultrasound instrument having a plurality of diagnostic modes, wherein access to the diagnostic modes is controlled through a gate flag registry, the gate flag registry configured to be modified through a verification procedure utilizing a secure means for extracting hidden bits from a keycode based on one or more unique system identifiers.

21. A method of operating a hand held ultrasound system comprising the steps of:
    (a) providing a balance body ultrasound system having an aperture and control elements, wherein the control elements are positioned such that the control elements can be operated using the thumb of a hand of a user, when the hand is inserted into the aperture;
    (b) inserting a first hand into an aperture of a balance body ultrasound system;
    (c) activating said ultrasound system;
    (d) operating said ultrasound system controls with said first hand;
    (e) manipulating a scan head with a second hand;
    (f) recording data from said scan head by operating said ultrasound system with said first hand; and
    (g) operating any system functions with said first hand wherein all operations of the balance body occur using a thumb of the first hand without the need to move the first hand to accomplish any desired operational controls.

22. The method as described in claim 21, wherein step (g) further comprises:
    (g1) typing information in on a touch screen using a user's free hand.

\* \* \* \* \*